United States Patent
Chelliah et al.

(10) Patent No.: US 8,022,088 B2
(45) Date of Patent: Sep. 20, 2011

(54) SUBSTITUTED BICYCLIC AND TRICYCLIC THROMBIN RECEPTOR ANTAGONISTS

(75) Inventors: Mariappan V. Chelliah, Edison, NJ (US); Samuel Chackalamannil, Califon, NJ (US); Yan Xia, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 19 days.

(21) Appl. No.: 11/769,018

(22) Filed: Jun. 27, 2007

(65) Prior Publication Data

US 2008/0004318 A1    Jan. 3, 2008

Related U.S. Application Data

(60) Provisional application No. 60/817,302, filed on Jun. 29, 2006.

(51) Int. Cl.
*A01N 43/40* (2006.01)
*A61K 31/44* (2006.01)
*C07D 405/00* (2006.01)

(52) U.S. Cl. ..................................... 514/337; 546/284.1
(58) Field of Classification Search .................. None
See application file for complete search history.

(56) References Cited

U.S. PATENT DOCUMENTS

| | | | |
|---|---|---|---|
| 6,063,847 A | 5/2000 | Chackalamannil et al. | |
| 6,303,646 B1 * | 10/2001 | Lu et al. .................. | 514/410 |
| 6,326,380 B1 | 12/2001 | Chackalamannil et al. | |
| 6,645,987 B2 * | 11/2003 | Chackalamannil et al. .. | 514/337 |
| 7,037,920 B2 | 5/2006 | Chackalamannil et al. | |
| 2003/0216437 A1 | 11/2003 | Chackalamannil et al. | |
| 2004/0152736 A1 | 8/2004 | Chackalamannil et al. | |

FOREIGN PATENT DOCUMENTS

| | | |
|---|---|---|
| WO | WO 94/03479 A1 | 2/1994 |
| WO | WO 01/96330 A2 | 12/2001 |
| WO | WO 03/033501 A1 | 4/2003 |
| WO | WO 2005/118576 A1 | 12/2005 |

OTHER PUBLICATIONS

Remingtons, 1980, pp. 420-425.*
Jordan, V.C. Nature Reviews: Drug Discovery, 2, 2003, p. 205.*
Dorwald F. Zaragoza. Side Reviews in Organic Synthesis: A guide to successful synthesis design, Weinheim: WILEY-VCH, Verlag, GMBH & Co. KGaA, 2005, Preface.*
Wolff et al. Burger's Medicinal Chemistry and Drug Discovery—Fifth Edition, New York: John Wiley & Songs, 1996, vol. 1, pp. 975-976.*
Vippagunta et al. Advanced Drug Delivery Reviews, 48, 2001, p. 18.*
Schaefer et al. Failure is an option: learning from unsuccessful proof-of-concept trials. Drug Discovery Today, 2008, 13 (21/22): 913-916.*
Horig et al. Review: From bench to clinic and back: Perspective on the 1$^{st}$ IQPC Translation Research Conference. Journal of Translational Medicine, 2004, 2(44).*
J.G. Cannon Nineteen in Bruger's Medicinal Chemistry and Drug Discovery, Fifth Edition, vol. 1: Principles and Practice, Wiley Interscience, 1995, pp. 783-802.*
Bensaid et al., "The Cannabinoid $CB_1$ Receptor Antagonist SR141716 Increases Acrp30 mRNA Expression in Adipose Tissue of Obese fa/fa Rats and in Cultured Adipocyte Cells", Molecular Pharmacology, 63(4): 908-914 (2003).
Bernatowicz et al., "Development of Potent Thrombin Receptor Antagonist Peptides", *J. Med. Chem.*, 39: 4879-4887 (1996).
Chackalamannil, "A Highly Efficient Total Synthesis of (+)-Himbacine", *J. Am. Chem. Soc.*, 118: 9812-9813 (1996).
Chackalamannil, "Discovery of Potent Orally Active Thrombin Receptor (Protease Activated Receptor 1) Antagonists as Novel Antithrombotic Agents", *J. Med. Chem.*, 48: 5884-5887 (2005).
Pertwee, "Pharmacology of Cannabinoid Receptor Ligands", *Current Medicinal Chemistry*, 6(8): 635-664 (1999).

* cited by examiner

*Primary Examiner* — Brandon Fetterolf
*Assistant Examiner* — Anna Pagonakis
(74) *Attorney, Agent, or Firm* — Mark W. Russell

(57) ABSTRACT

Substituted bicyclic and tricyclic modified himbacine derivative of the formula:

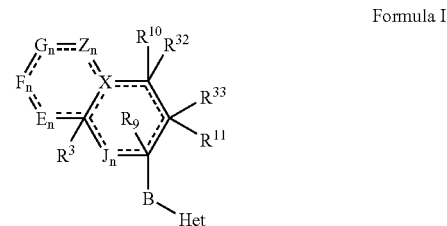

Formula I or a pharmaceutically acceptable salt or solvate of said compound wherein ----- represents an optional double bond and wherein $E_n, F_n, G_n, Z_n, J_n, X, R^3, R^9, R^{10}, R^{11}, R^{32}, R^{33}$, B and Het are herein defined are disclosed, as well as pharmaceutical compositions containing them and a method of treating diseases associated with thrombosis, atherosclerosis, restenosis, hypertension, angina pectoris, arrhythmia, heart failure, and cancer by administering said compounds. Combination therapy with other agents is also claimed.

10 Claims, No Drawings

SUBSTITUTED BICYCLIC AND TRICYCLIC THROMBIN RECEPTOR ANTAGONISTS

RELATED APPLICATIONS

This application claims priority to provisional application U.S. Ser. No. 60/817,302, filed Jun. 29, 2006, herein incorporated by reference.

BACKGROUND OF THE INVENTION

The present invention relates to himbacine derivatives, which can be useful as thrombin receptor antagonists in the treatment of diseases associated with thrombosis, atherosclerosis, restenosis, hypertension, angina pectoris, arrhythmia, heart failure, cerebral ischemia, stroke, neurodegenerative diseases and cancer. Thrombin receptor antagonists are also known as protease activated receptor-1 (PAR-1) antagonists. The compounds of the invention also can be useful as cannabinoid ($CB_2$) receptor inhibitors for the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis. The invention also relates to pharmaceutical compositions comprising said compounds.

Thrombin is known to have a variety of activities in different cell types. Thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al., J. Med. Chem., 39 (1996), p. 4879-4887, tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor antagonists are also disclosed in WO 94/03479, published Feb. 17, 1994.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee. Curr. Med. Chem. 6(8), (1999), 635; M. Bensaid, Molecular Pharmacology, 63 (4), (2003), 908.).

Himbacine, a piperidine alkaloid of the formula

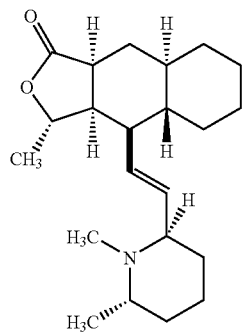

has been identified as a muscarinic receptor antagonist. The total synthesis of (+)-himbacine is disclosed in Chackalamannil et al., J. Am. Chem. Soc., 118 (1996), p. 9812-9813. Properties of himbacine derived compounds that are thrombin receptor antagonists have been described. (Chackalamannil et. al. J. Med. Chem., 48 (2005), 5884-5887.)

Substituted tricyclic thrombin receptor antagonists are disclosed in U.S. Pat. Nos. 6,063,847, 6,326,380 and U.S. Ser. Nos. 09/880,222 (WO 01/96330), 10/271,715, and 10/412,982.

SUMMARY OF THE INVENTION

The present invention relates to compounds represented by the formula I:

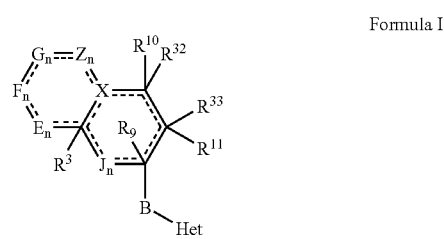

Formula I or a pharmaceutically acceptable salt, solvate, or ester of said compound, wherein ----- represents a double bond or a single bond, as permitted by the valency requirement; with the proviso that $R^{10}$ or $R^{11}$ are absent when the carbon to which $R^{10}$ or $R^{11}$ are attached is part of a double bond;

B is —$(CH_2)_{n3}$—, —$(CH_2)$—O—, —$(CH_2)S$—, —$(CH_2)$—$NR^6$—, —$C(O)NR^6$—, —$NR^6C(O)$—,

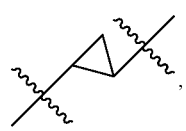

—$(CH_2)_{n4}CR^{12}$=$CR^{12a}(CH_2)_{n5}$— or —$(CH_2)_{n4}C$≡$C(CH_2)_{n5}$—, wherein $n_3$ is 0-5, $n_4$ and $n_5$ are independently 0-2, and $R^{12}$ and $R^{12a}$ are independently selected from the group consisting of hydrogen, alkyl and halogen;

E, F, G, Z, and J are independently selected from the group consisting of —NR($R^1$)—, $NR^2$,

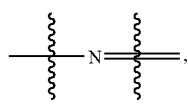

—(CR$^1$R$^2$)—, —O—,

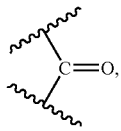

—S—, —S(O)—, —S(O)$_2$— and

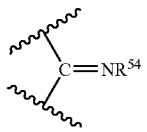

with the provisos that selection of E, F, G, Z, and J does not result in adjacent oxygen or sulfur atoms and that at least one carbon atom appear between said oxygen, nitrogen or sulfur atoms;

X is 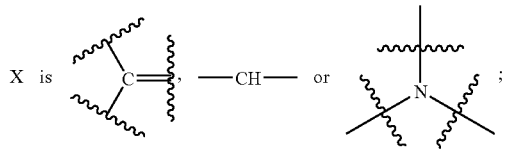

each n is 0, 1 or 2 with the proviso that all n variables cannot be 0;

Het is a mono-, bi- or tricyclic heteroaromatic group of 5 to 14 atoms comprised of 1 to 13 carbon atoms and 1 to 4 heteroatoms independently selected from the group consisting of N, O and S, with the proviso that there are no adjacent oxygen or sulfur atoms present in the heteroaromatic group, wherein a ring nitrogen can form an N-oxide or a quaternary group with an alkyl group, wherein Het is attached to B by a carbon atom ring member, and wherein the Het group is substituted by 1 to 4 moieties, W, wherein each W is independently selected from the group consisting of
hydrogen,
alkyl,
fluoroalkyl, difluoroalkyl, trifluoroalkyl, haloalkyl, dihaloalkyl, trihaloalkyl,
cycloalkyl, cycloalkyl substituted by alkyl, alkenyl, or alkynyl,
heterocycloalkyl, heterocycloalkyl substituted by alkyl, alkenyl, or alkynyl,
R$^{21}$-arylalkyl, R$^{21}$-aryl-alkenyl,
heteroaryl, heteroarylalkyl, heteroarylalkenyl,
hydroxyalkyl, dihydroxyalkyl,
aminoalkyl, alkylaminoalkyl, di-(alkyl)-aminoalkyl, thioalkyl,
alkoxy, alkenyloxy,
halogen,
—NR$^4$R$^5$,
—SH,
—CN,
—OH,
—C(O)OR$^{17}$, —COR$^{16}$, —OS(O$_2$)CF$_3$, —CH$_2$OCH$_2$CF$_3$, alkylthio,
—C(O)NR$^4$R$^5$,
—OCHR$^6$-phenyl,
phenoxyalkyl,
—NHCOR$^{16}$,
—NHSO$_2$R$^{16}$,
biphenyl,
—OC(R$^6$)$_2$COOR$^7$, —OC(R$^6$)$_2$C(O)NR$^4$R$^5$,
alkoxy substituted by alkyl, amino or —NHC(O)OR$^{17}$,
aryl,
aryl substituted by 1 to 3 substituents independently selected from the group consisting of alkyl, halogen, alkoxy, methylenedioxy, carboxylic acid, carboxamide, amine, urea, amide, sulfonamide, —CN, —CF$_3$, —OCF$_3$, —OH, alkylamino-, di-(alkyl)amino-, —NR$^{25}$R$^{26}$alkyl-, hydroxyalkyl-, —C(O)OR$^{17}$, —COR$^{17}$, —NHCOR$^{16}$, —NHS(O)$_2$R$^{16}$, —NHS(O)$_2$CH$_2$CF$_3$, —C(O)NR$^{25}$R$^{26}$, NR$^{25}$R$^{26}$, —S(O)R$^{13}$, —S(O)$_2$R$^{13}$ and —SR$^{13}$,
or alkyl optionally substituted with —NR$^1$R$^2$, —NR$^1$COR$^2$, —NR$^1$CONR$^1$R$^2$,
—NR$^1$C(O)OR$^2$, —NR$^1$S(O)$_2$R$^2$, —NR$^1$S(O)$_2$NR$^1$R$^2$, —C(O)OH, —C(O)OR$^1$, —CONR$^1$R$^2$heteroaryl, hydroxyalkyl, alkyl, —S(O)$_2$-alkyl, —C(O)NR$^4$R$^5$ or heteroaryl; wherein adjacent carbons on the Het ring can optionally form a ring with a methylenedioxy group;

R$^1$ and R$^2$ are independently selected from the group consisting of hydrogen, halogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, amine, aminoalkyl, aryl, thiohydroxy, CN, and thioalkyl; or R$^1$ and R$^2$ when attached to nitrogen, taken together, form a mono or bicyclic heterocyclic ring of 4 to 10 atoms, with 1-3 heteroatoms selected from —O—, —N—, —S—, —S(O)—, —S(O)$_2$— and

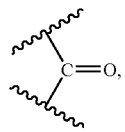

with the proviso that S and O ring atoms are not adjacent to each other, where said heterocyclic ring is unsubstituted or substituted with one or more groups independently selected from alkyl, halogen, hydroxy, alkoxy, aryloxy and arylalkoxy;

R$^3$ is R$^1$, fluoroalkoxy, difluoroalkoxy, trifluoroalkoxy, cycloalkyloxy, alkenyloxy, alkoxy, arylalkoxy, arylalkenyloxy, heteroarylalkoxy, heteroarylalkenyloxy, hydroxyalkoxy, alkoxyalkoxy, aminoalkoxy, aryloxy or thioalkoxy, R$^6$ is hydrogen, alkyl or phenyl;

R$^7$ is hydrogen or alkyl;

each R$^{13}$ is independently selected from hydrogen, alkyl, cycloalkyl, haloalkyl, halogen, —(CH$_2$)$_{n6}$NHC(O)OR$^{16b}$, —(CH$_2$)$_{n6}$NHC(O)R$^{16b}$, —(CH$_2$)$_{n6}$NHC(O)NR$^4$R$^5$, —(CH$_2$)$_{n6}$NHSO$_2$R$^{16}$, —(CH$_2$)$_{n6}$NHSO$_2$NR$^4$R$^5$, and —(CH$_2$)$_{n6}$C(O)NR$^{28}$R$^{29}$, where n$_6$ is 0-4;

each R$^{14}$ is independently selected from the group consisting of hydrogen, alkyl, —OH, alkoxy, arylalkyl, heteroaryl, heteroarylalkyl, heterocyclyl, heterocyclylalkyl, halogen, haloalkyl, —(CH$_2$)$_{n6}$NHC(O)OR$^{16b}$, —(CH$_2$)$_{n6}$NHC(O)R$^{16b}$, —(CH$_2$)$_{n6}$NHC(O)NR$^4$R$^5$, —(CH$_2$)$_{n6}$NHSO$_2$R$^{16}$, —(CH$_2$)$_{n6}$NHSO$_2$NR$^4$R$^5$, and —(CH$_2$)$_{n6}$C(O)NR$^{28}$R$^{29}$ where n$_6$ is 0-4; where R$^4$ and R$^5$ are independently selected from the group consisting of hydrogen, alkyl, phenyl, benzyl and cycloalkyl, or R$^4$ and R$^5$ together can form a ring with the nitrogen to which they are attached, wherein said ring formed by R$^4$ and R$^5$ is optionally substituted with =O, OH, OR$^1$ or —C(O)OH; or R$^{13}$ and R$^4$ taken together form a spirocyclic or a heterospirocyclic ring of 3-6 ring atoms, wherein said heterospirocyclic ring contains 2 to 5 carbon ring atoms and 1 or 2 hetero ring atoms selected from the group consisting of O, S and N;

R$^{16}$ is independently selected from the group consisting of hydrogen, alkyl, phenyl and benzyl;

R$^{16a}$ is independently selected from the group consisting of hydrogen, alkyl, phenyl and benzyl;

R$^{16b}$ is hydrogen, alkoxy, alkyl, alkoxyalkyl-, R$^{22}$—O—C(O)-alkyl-, cycloalkyl, R$^{21}$-aryl, R$^{21}$-arylalkyl, haloalkyl, alkenyl, halo substituted alkenyl, alkynyl, halo substituted alkynyl, R$^{21}$-heteroaryl, (R$^{21}$-heteroaryl)-alkyl-, (R$^{21}$-heterocycloalkyl)-alkyl-, R$^{28}$R$^{29}$N-alkyl-, R$^{28}$R$^{29}$N—C(O)-alkyl-, R$^{28}$R$^{29}$N—C(O)O-alkyl-, R$^{28}$OC(O)N(R$^{29}$)-alkyl-, R$^{28}$S(O)$_2$N(R$^{29}$)-alkyl-, R$^{28}$R$^{29}$N—C(O)—N(R$^{29}$)-alkyl-, R$^{28}$R$^{29}$N—S(O)$_2$N(R$^{29}$)-alkyl-, R$^{28}$—C(O)N(R$^{29}$)-alkyl-, R$^{28}$R$^{29}$N—S(O)$_2$-alkyl-, HOS(O)$_2$-alkyl-, (OH)$_2$P(O)$_2$-alkyl-, R$^{28}$—S—alkyl-, R$^{28}$—S(O)$_2$-alkyl- or hydroxyalkyl;

R$^{17}$ is independently selected from the group consisting of hydrogen, alkyl, phenyl and benzyl;

R$^{18}$ and R$^{19}$ are hydrogen, alkyl, aryl, R$^{21}$-aryl, heteroaryl, cycloalkyl, heterocyclyl, alkoxyalkyl, haloalkoxyalkyl, aryloxyalkyl, arylalkoxyalkyl, heteroaryloxyalkyl, heteroarylalkoxyalkyl, cycloalkyloxyalkyl, (heterocyclyl)alkyloxyalkyl, alkoxyalkyloxyalkyl, —S(O)$_2$-alkyl, —C(NH)NR$^1$R$^2$ or alkyl substituted with one or two moieties selected from cycloalkyl, halogen, hydroxy, —NR$^1$R$^2$, —NR$^1$C(O)R$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$ and —C(O)NR$^1$R$^2$; or R$^{18}$ and R$^{19}$ together with the nitrogen to which they are attached, form a mono or bicyclic heterocyclic ring of 4 to 10 atoms, having 1-3 hetero ring atoms selected from —O—, —N—, —S—, —S(O)—, —S(O)$_2$ and —C(O)—, with the proviso that S and O atoms are not adjacent to each other, the ring being unsubstituted or substituted with one or more groups selected from alkyl, halogen, hydroxy, alkoxy, aryloxy, arylalkoxy, —NR$^1$R$^2$, —NR$^1$COR$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OR$^1$, —CONR$^1$R$^2$ and alkyl substituted with —NR$^1$R$^2$, —NR$^1$COR$^2$, —NR$^1$CONR$^1$R$^2$, —NR$^1$C(O)OR$^2$, —NR$^1$S(O)$_2$R$^2$, —NR$^1$S(O)$_2$NR$^1$R$^2$, —C(O)OR$^1$ or —CONR$^1$R$^2$, R$^{21}$ is 1 to 3 moieties and each R$^{21}$ is independently selected from the group consisting of hydrogen, —CN, —CF$_3$, —OCF$_3$, halogen, —NO$_2$, alkyl, —OH, alkoxy, alkylamino-, di-(alkyl)amino-, —NR$^{25}$R$^{26}$alkyl-, hydroxyalkyl-, —C(O)OR$^{17}$, —COR$^{17}$, —NHCOR$^{16}$, —NHS(O)$_2$R$^{16}$, —C(NH)—NH$_2$, —NHS(O)$_2$CH$_2$CF$_3$, —C(O)NR$^{25}$R$^{26}$, —NR$^{25}$—C(O)—NR$^{25}$R$^{26}$, —S(O)R$^{16}$, —S(O)$_2$R$^{16}$, —SR$^{16}$; —SO$_2$NR$^4$R$^5$ and —CONR$^4$, R$^5$; or two adjacent R$^{21}$ moieties can form a methylenedioxy group;

R$^{22}$ is hydrogen, alkyl, phenyl, benzyl, —COR$^{16}$; —CONR$^{18}$R$^{19}$, —COR$^{23}$—S(O)R$^{31}$, —S(O)$_2$R$^{31}$, —S(O)$_2$NR$^{24}$R$^{25}$ or —C(O)OR$^{27}$;

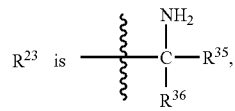

R$^{23}$ is wherein R$^{35}$ and R$^{36}$ are independently selected from the group consisting of hydrogen, alkyl, and R$^{37}$-substituted alkyl, wherein R$^{37}$ is selected from the group consisting of HO—, HS—, CH$_2$S—, —NH$_2$, phenyl, p-hydroxyphenyl and indolyl; or R$^{23}$ is alkyl; haloalkyl; alkenyl; haloalkenyl; alkynyl; cycloalkyl; cycloalkylalkyl; cycloalkyl substituted by 1 to 3 substituents selected from the group consisting of alkoxyalkyl, alkyl, halogen, hydroxy, alkoxy, aryloxy, arylalkoxy, —NR$^1$R$^2$, —NR$^1$C(O)R$^2$—NR$^1$C(O)NR$^1$R$^2$—NR$^1$C(O)OR$^2$—NR$^1$S(O)$_2$R$^2$—NR$^1$S(O)$_2$NR$^1$R$^2$, —C(O)OR$^1$ and —CONR$^1$, R$^2$; aryl; aralkyl; heteroaryl; heterocycloalkyl; alkyl substituted with —NR$^1$R$^2$, —NR$^1$COR$^2$, —NR$^1$CONR$^1$R$^2$, —NR$^1$C(O)OR$^2$, —NR$^1$S(O$_2$)R$^2$, —NR$^1$S(O$_2$)NR$^1$R$^2$, —C(O)OR$^1$, —CONR$^1$R$^2$ and —SO$_3$H;

R$^{24}$, R$^{25}$ and R$^{26}$ are independently selected from the group consisting of hydrogen, alkyl, haloalkyl, alkenyl, alkynyl, aryl, aralkyl, cycloalkyl, halocycloalkyl, alkoxyalkyl, hydroxy and alkoxy;

R$^{27}$ is 1 to 3 moieties and each R$^{27}$ is selected from the group consisting of hydrogen, alkyl, and cycloalkyl, wherein R$^{27}$ is optionally substituted with —OH, —C(O)OH, halogen and alkoxy;

R$^{28}$ and R$^{29}$ are independently selected from the group consisting of hydrogen, alkyl, alkoxy; arylalkyl, heteroaryl, heteroarylalkyl, hydroxyalkyl, alkoxyalkyl, heterocyclyl, heterocyclylalkyl, and haloalkyl; or R$^{28}$ and R$^{29}$ taken together form a spirocyclic or a heterospirocyclic ring having 3-6 ring atoms;

R$^{32}$ and R$^{33}$ are independently selected from the group consisting of hydrogen, R$^{34}$-alkyl, R$^{34}$-alkenyl, R$^{34}$-alkynyl, R$^{40}$-heterocycloalkyl, R$^{38}$-aryl, R$^{38}$-aralkyl, R$^{42}$-cycloalkyl, R$^{42}$-cycloalkenyl, —OH, —OC(O)R$^{43}$—C(O)OR$^{43}$, —C(O)R$^{43}$—O(NR$^{43}$R$^{44}$, —NR$^{43}$R$^{44}$, —NR$^{43}$C(O)R$^{44}$, —NR$^{43}$C(O)R$^{44}$, —NR$^{43}$C(O)NR$^4$R$^4$R$^4$—NHS(O)$_2$R$^{43}$, —OC(O)NR$^{43}$R$^{44}$, R$^{37}$-alkoxy, R$^{37}$-alkynyloxy, R$^{37}$-alkynyloxy, R$^{40}$-heterocycloalkyloxy, R$^{42}$-cycloalkyloxy, R$^{42}$-cycloalkenyloxy, R$^{42}$-cycloalkyl-NH—, —NHSO$_2$NHR$^{16}$ and —CH(=NOR$^{17}$);

or R$^{32}$ and R$^{33}$ are combined to form a ring structure Q, below

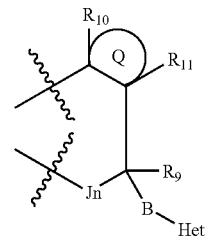

where

R$^9$ is hydrogen, OH, alkoxy, halogen or haloalkyl;

Q is fused R-substituted aryl, R-substituted heteroaryl, R-substituted heterocyclic ring of 4-8 atoms containing 1-3 heteroatoms selected from O, S, S(O), S(O)$_2$ and NR$^{22}$ with the proviso that S and O cannot be adjacent to one another; or Q is

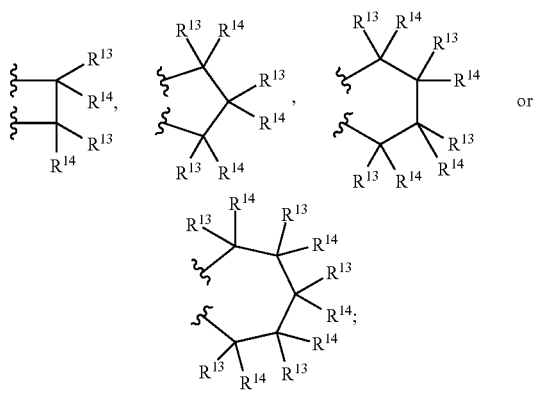

wherein $R^{10}$ and $R^{11}$ are independently selected from the group consisting of $R^1$ and —$OR^1$, provided that when ring Q is aromatic and the carbon atoms bearing $R^{10}$ and $R^{11}$ are connected by a double bond, $R^{10}$ and $R^{11}$ are absent;

R is 1 to 5 moieties and each R is independently selected from the group consisting of hydrogen, alkyl, halogen, hydroxy, amino, alkylamino, dialkylamino, alkoxy, —$COR^{16}$, —$C(O)R^{17}$, —$C(O)NR^4R^5$, —$SOR^{16}$, —$S(O_2)R^{16}$, —$NR^{16}COR^{16a}$, —$NR^{16}C(O)OR^{16a}$, —$NR^{16}CONR^4R^5$, —$NR^{16}S(O_2)NR^4R^5$, fluoroalkyl, difluoroalkyl, trifluoroalkyl, cycloalkyl, alkenyl, arylalkyl, arylalkenyl, heteroarylalkyl, heteroarylalkenyl, hydroxyalkyl, aminoalkyl, aryl and thioalkyl;

$R^{34}$ is 1 to 3 moieties and each $R^{34}$ is independently selected from the group consisting of hydrogen, halogen, —OH, alkoxy, $R^{47}$-aryl, alkyl-C(O)—, alkenyl-C(O)—, alkynyl-C(O)—, heterocycloalkyl, $R^{39}$-cycloalkyl, $R^{39}$-cycloalkenyl, —$OC(O)R^{43}$, —$C(O)OR^{43}$, —$C(O)R^{43}$, —$C(O)NR^{43}R^{44}$, —$NR^{43}R^{44}$, —$NR^{43}C(O)R^{44}$, —$NR^{43}C(O)NR^{44}R^{45}$, —$NHSO_2R^{43}$, —$OC(O)NR^{43}R^{44}$, $R^{34}$-alkenyloxy, $R^{34}$-alkynyloxy, $R^{40}$-heterocycloalkyloxy, $R^{42}$-cycloalkyloxy, $R^{42}$-cycloalkenyloxy, $R^{42}$-cycloalkyl-NH—, —$NHSO_2NHR^{16}$ and —$CH(=NOR^{17})$;

$R^{38}$ is 1 to 3 moieties and each $R^{38}$ is independently selected from the group consisting of hydrogen, heterocycloalkyl, halogen, —$C(O)OR^{48}$1-CN, —$C(O)NR^{49}R^{50}$, —$NR^{51}C(O)R^{52}$, —$OR^{48}$, cycloalkyl, cycloalkylalkyl, alkylcycloalkylalkyl, haloalkylcycloalkylalkyl, hydroxyalkyl, alkoxyalkyl, and $R^{52}$-heteroaryl; or two $R^{38}$ groups on adjacent ring carbons form a fused methylenedioxy group;

$R^{39}$ is 1 to 3 moieties and each $R^{39}$ is independently selected from the group consisting of hydrogen, halogen and alkoxy;

$R^{40}$ is 1 to 3 moieties and each $R^{40}$ is independently selected from the group consisting of hydrogen, $R^{41}$-alkyl, $R^{41}$-alkenyl and $R^{41}$-alkynyl;

$R^{41}$ is hydrogen, —OH or alkoxy;

$R^{42}$ is 1 to 3 moieties and each $R^{42}$ is independently selected from the group consisting of hydrogen, alkyl, —OH, alkoxy and halogen;

$R^{43}$, $R^{44}$ and $R^{45}$ are independently selected from the group consisting of hydrogen, alkyl, alkoxyalkyl, $R^{38}$-arylalkyl, $R^{46}$-cycloalkyl, $R^{53}$-cycloalkylalkyl, $R^{38}$-aryl, heterocycloalkyl, heteroaryl, heterocycloalkylalkyl and heteroarylalkyl;

$R^{46}$ is hydrogen, alkyl, hydroxyalkyl or alkoxy;

$R^{47}$ is 1 to 3 moieties and each $R^{47}$ is independently selected from the group consisting of hydrogen, alkyl, —OH, halogen, —CN, alkoxy, trihaloalkoxy, alkylamino, di(alkyl)amino, —$OCF_3$, hydroxyalkyl, —CHO, —C(O)alkylamino, —C(O)di(alkyl)amino, —$NH_2$, —NHC(O)alkyl and —N(alkyl)C(O)alkyl;

$R^{48}$ is hydrogen, alkyl, haloalkyl, dihaloalkyl or trifluoroalkyl;

$R^{49}$ and $R^{50}$ are independently selected from the group consisting of hydrogen, alkyl, aralkyl, phenyl and cycloalkyl, or $R^{49}$ and $R^{50}$ together are —$(CH_2)_4$—, —$(CH_2)_5$— or —$(CH_2)_2$—$NR^{39}$—$(CH_2)_2$— and form a ring with the nitrogen to which they are attached;

$R^{51}$ and $R^{52}$ are independently selected from the group consisting of hydrogen, alkyl, aralkyl, phenyl and cycloalkyl, or $R^{51}$ and $R^{52}$ in the group —$NR^{39}C(O)R^{40}$, together with the nitrogen atoms to which they are attached, form a cyclic lactam having 5-8 ring members;

$R^{53}$ is hydrogen, alkoxy, —$SOR^{16}$, —$SO_2R^{17}$, —C(O)$OR^{17}$, —C(O)$NR^{18}R^{19}$, alkyl, halogen, fluoroalkyl, difluoroalkyl, trifluoroalkyl, cycloalkyl, alkenyl, aralkyl, arylalkenyl, heteroarylalkyl, heteroarylalkenyl, hydroxyalkyl, aminoalkyl, aryl, thioalkyl, alkoxyalkyl or alkylaminoalkyl; and $R^{54}$ is selected from the group consisting of hydrogen; alkyl; fluoroalkyl; difluoroalkyl; trifluoroalkyl; cycloalkyl; cycloalkyl substituted by 1 to 3 substituents selected from the group consisting of alkoxyalkyl, alkyl, halogen, hydroxy, alkoxy, aryloxy, arylalkoxy, —$NR^1R^2$, —$NR^1C(O)R^2$, —$NR^1C(O)NR^1R^2$, —$NR^1C(O)OR^2$, —$NR^1S(O)_2R^2$, —$NR^1S(O)_2NR^1$, $R^2$—C(O)OH, —C(O)$OR^1$ and —CONR$^1R^2$; alkenyl; alkoxy; arylalkyl; arylalkenyl; heteroarylalkyl; heteroarylalkenyl; hydroxy; alkoxy; hydroxyalkyl; alkoxyalkyl; aminoalkyl; aryl; heteroaryl; thioalkyl and alkyl substituted by 1 to 3 subsituents selected from the group consisting of urea, sulfonamide, carboxamide, carboxylic acid, carboxylic ester and sulfonyl urea.

Pharmaceutical compositions comprising at least one compound of formula I and at least one pharmaceutically acceptable carrier are also provided.

The compounds of the present invention can be useful as Thrombin receptor antagonists, also known as PAR-1 antagonists, or as cannabinoid ($CB_2$) receptor antagonists. Thrombin receptor antagonist compounds of the present invention can have anti-thrombotic, anti-platelet aggregation, anti-atherosclerotic, anti-restenotic, anti-coagulant, and/or anti-inflammatory activity. $CB_2$ receptor inhibitor compounds of the present invention can be useful for the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

Compounds of the invention can be useful for the treatment of thrombosis, atherosclerosis, restenosis, hypertension, angina pectoris, angiogenesis related disorders, arrhythmia, a cardiovascular or circulatory disease or condition, heart failure, acute coronary syndrome (ACS), myocardial infarction, glomerulonephritis, thrombotic stroke, thromboembolytic stroke, peripheral vascular diseases, deep vein thrombosis, venous thromboembolism, a cardiovascular disease associated with hormone replacement therapy, disseminated intravascular coagulation syndrome, cerebral infarction, as well as other disorders in which thrombin and its receptor play a pathological role.

In particular, compounds of the present invention are used to treat acute coronary syndrome, myocardial infarction or thrombotic stroke.

Compounds of the present invention can also be used in a method to treat or prevent a condition associated with cardiopulmonary bypass surgery (CPB) comprising administering an effective amount of at least one thrombin receptor antagonist to a subject of said surgery. CPB surgery includes coronary artery bypass surgery (CABG), cardiac valvular repair and replacement surgery, pericardial and aortic repair surgeries. In particular, the present invention relates to a method of treating or preventing a condition associated with CABG surgery comprising administering an effective amount of at least one thrombin receptor antagonist to a subject of said surgery. The conditions associated with CABG are selected from the group consisting of: bleeding; thrombotic vascular events such as thrombosis, restenosis; vein graft failure; artery graft failure; atherosclerosis, angina pectoris; myocardial ischemia; acute coronary syndrome myocardial infarction; heart failure; arrhythmia; hypertension; transient ischemic attack; cerebral function impairment; thromboembolic stroke; cerebral ischemia; cerebral infarction; thrombophlebitis; deep vein thrombosis; and, peripheral vascular disease.

Certain embodiments of this invention also relate to a method of using an effective amount of at least one compound of Formula I in combination with one or more additional agents for the treatment of thrombosis, atherosclerosis, restenosis, hypertension, angina pectoris, angiogenesis related disorders, arrhythmia, a cardiovascular or circulatory disease or condition, heart failure, acute coronary syndrome (ACS), myocardial infarction, glomerulonephritis, thrombotic stroke, thromboembolytic stroke, peripheral vascular diseases, deep vein thrombosis, venous thromboembolism, a cardiovascular disease associated with hormone replacement therapy, disseminated intravascular coagulation syndrome, cerebral infarction, It is contemplated that a combination of this invention may be useful in treating more than one of the diseases listed.

Pharmaceutical compositions comprising a therapeutically effective amount of a combination of at least one compound of formula I and at least one additional cardiovascular agent in a pharmaceutically acceptable carrier are also provided.

It is further contemplated that the combination of the invention can be provided as a kit comprising in a single package at least one compound of formula I in a pharmaceutical composition, and at least one separate pharmaceutical composition comprising a cardiovascular agent.

DETAILED DESCRIPTION

In one embodiment, the present invention provides compounds represented by structural formula I, or pharmaceutically acceptable salt thereof, wherein the various moieties are as described as above.

For compounds of Formula I, preferred embodiments of the compounds of formula I are as follows;

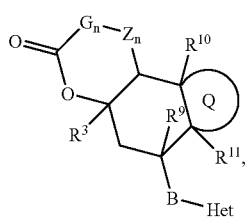

Ia

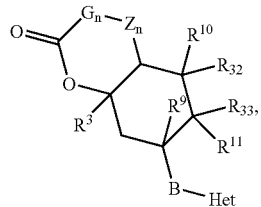

IIa

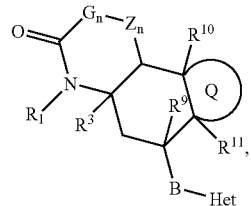

Ib

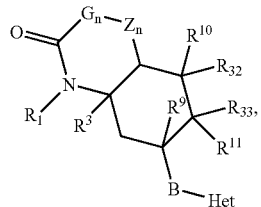

IIb

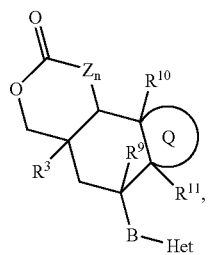

Ic

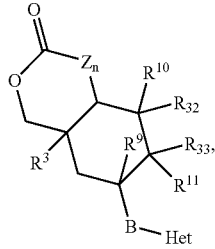

IIc

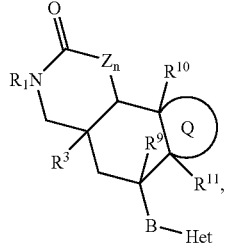

Id

-continued
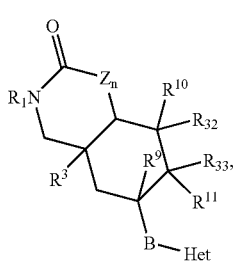
IId
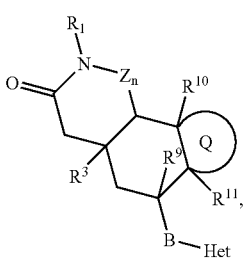
Ie
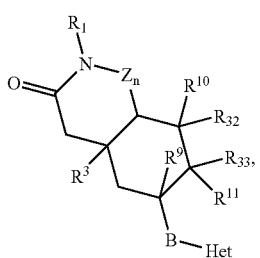
IIe
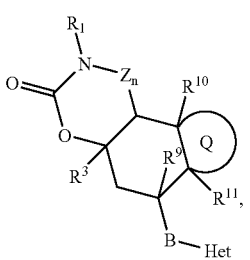
If
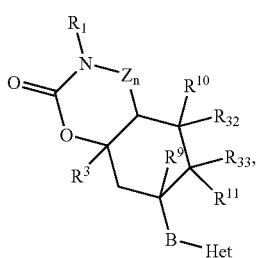
IIf
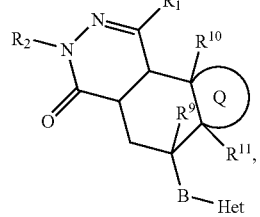
Ig
-continued
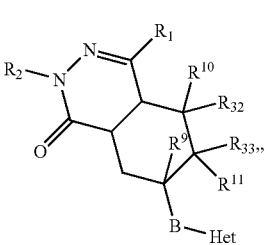
IIg
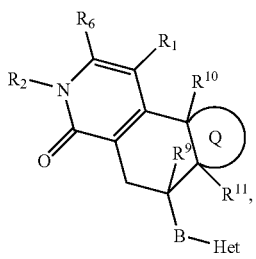
Ih
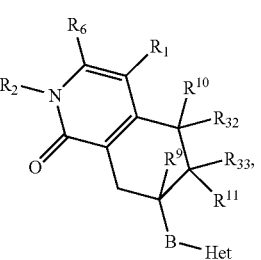
IIh
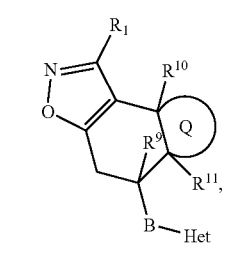
Ii
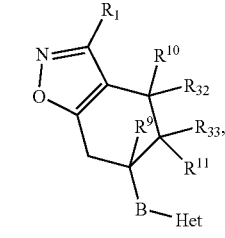
IIi
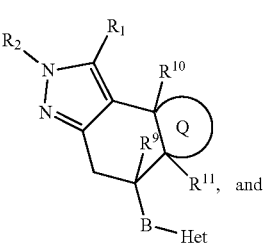
Ij
and -continued

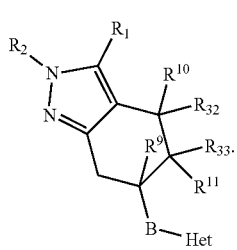
IIj

Additional preferred embodiments of the compounds of formula I are as follows:

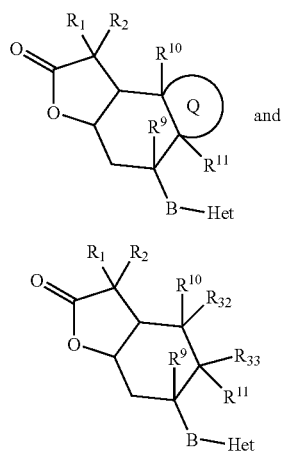
Ik

IIk

In another embodiment, in Formula I, $R^{32}$ and $R^{33}$ are combined to form the ring structure Q.

In another embodiment, in formula I,

Q is

In another embodiment, in formula I,

Q is

In another embodiment, in formula I, $R^{32}$ and $R^{33}$, which can be the same or different, are each alkyl.

In another embodiment, in formula I, $R^{32}$ and $R^{33}$, which can be the same or different, are each methyl.

In another embodiment, in formula I,

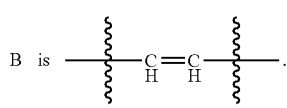
B is

In another embodiment, in formula I Het is unsubstituted pyridyl.

In another embodiment, in formula I Het is pyridyl substituted with W, wherein said W is aryl substituted with at least one —CN or at least one halogen.

In another embodiment, in formula I Het is pyridyl substituted with W, wherein said W is phenyl, which can be unsubstituted or substituted with at least one moiety, which can be the same or different, wherein said moiety is independently selected from the group consisting —CN or halogen.

In another embodiment, in formula I $E_n$ is $N(R^1)$—, —$CO_2$—,

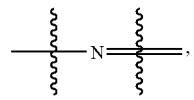

—O—, or

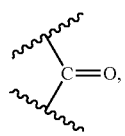

wherein n is 1.

In another embodiment, in formula I $F_n$ is $N(R^1)$—,

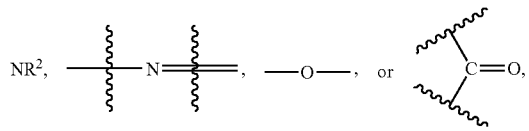
$NR^2$, , —O—, or wherein n is 1.

In another embodiment, in formula I, $G_n$ is

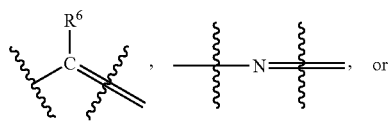
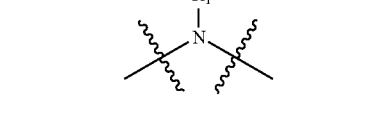

wherein $R^6$ and $R^1$ are each hydrogen, alkyl or phenyl, and further wherein n is 1.

In another embodiment, in formula I, $G_n$ is $G_0$.
In another embodiment, in formula I $Z_n$ is

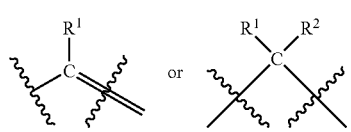

wherein n is 1.

In another embodiment, in formula I $Z_n$ is $CH_2$—, wherein n is 1.

In another embodiment, in formula I $J_n$ is —$CH_2$—, wherein n is 1.

In another embodiment, in formula I X is

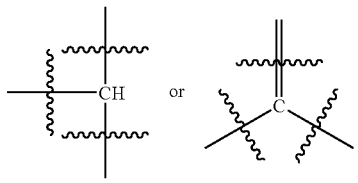

In another embodiment, in formula I $R^3$, $R^9$, $R^{10}$ and $R^{11}$ are H.

In another embodiment, this invention discloses a compound of the Formula:

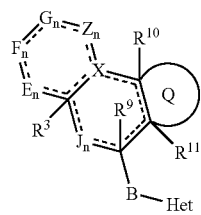

or a pharmaceutically acceptable salt, solvate, ester, or prodrug thereof, wherein Q is

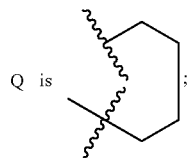

Het is W-substituted pyridyl;

W is phenyl substituted by at least one halogen or at least one cyano;

B is 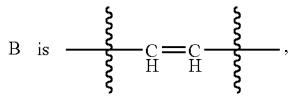, $F_n$ is 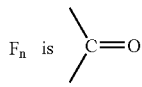

wherein n is 1;

$E_n$ is —O—, wherein n is 1;

$G_n$ is $G_0$ $J_n$ is —CH$_2$—, wherein n is 1;

$Z_n$ is —CH$_2$—, wherein n is 1;

X is 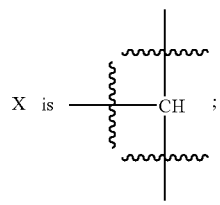;

$R^3$, $R^9$, $R^{10}$ and $R^{11}$ are H.

In another embodiment, this invention discloses a compound of the Formula:

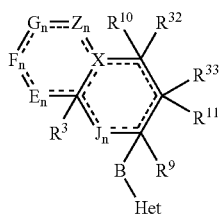

or a pharmaceutically acceptable salt, solvate, ester, or prodrug thereof wherein Het is W-substituted pyridyl;

W is phenyl substituted by at least one halogen or at least one cyano;

B is 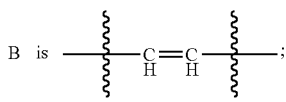;

$F_n$ is 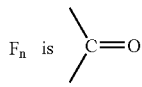

wherein n is 1;

$E_n$ is —O—, wherein n is 1;

$G_n$ is $G_0$ $J_n$ is —CH$_2$—, wherein n is 1;

$Z_n$ is —CH$_2$—, wherein n is 1;

X is 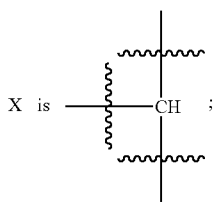;

$R^{32}$ and $R^{33}$ are each methyl;

$R^3$, $R^9$, $R^{10}$ and $R^{11}$ are H.

In another embodiment, this invention discloses a compound of the Formula:

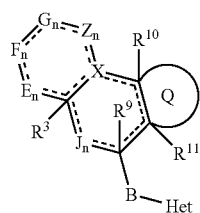

or a pharmaceutically acceptable salt, solvate, ester, or prodrug thereof, wherein Q is 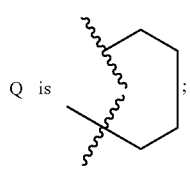;

Het is W-substituted pyridyl;

W is phenyl substituted by at least one halogen or at least one cyano;

B is 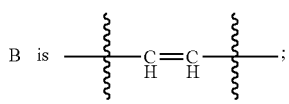;

$F_n$ is —O—, wherein n is 1;
$E_n$ is —CH$_2$—, wherein n is 1;

$G_n$ is 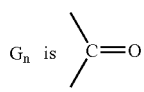

wherein n is 1
$J_n$ is —CH$_2$—, wherein n is 1;
$Z_n$ is —CH$_2$—, wherein n is 1;

X is 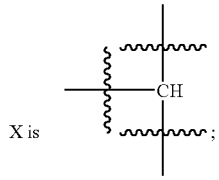;

and
$R^3$, $R^9$, $R^{10}$ and $R^{11}$ are H.

In another embodiment, this invention discloses a compound of the Formula:

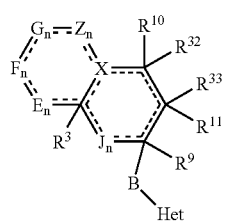

or a pharmaceutically acceptable salt, solvate, ester, or prodrug thereof, wherein Het is W-substituted pyridyl;

W is phenyl substituted by at least one halogen or at least one cyano;

B is 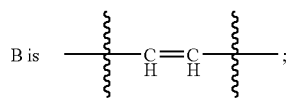;

$F_n$ is —O—, wherein n is 1;
$E_n$ is —CH$_2$—, wherein n is 1;

$G_n$ is 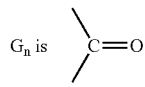

wherein n is 1
$J_n$ is —CH$_2$—, wherein n is 1;
$Z_n$ is —CH$_2$—, wherein n is 1;

X is 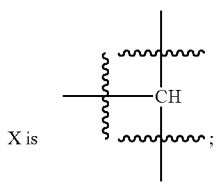;

$R^3$, $R^9$, $R^{10}$ and $R^{11}$ are H; and
$R^{32}$ and $R^{33}$ are each methyl.

In another embodiment, this invention discloses a compound of the Formula:

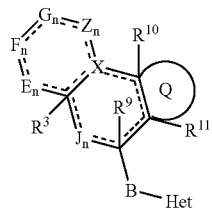

or a pharmaceutically acceptable salt, solvate, ester, or prodrug thereof, wherein Q is ;

Het is W-substituted pyridyl;

W is phenyl substituted by at least one halogen or at least one cyano;

B is 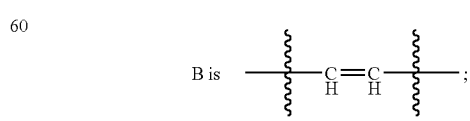;

$E_n$ is —O—, wherein n is 1;
$G_n$ is —CH$_2$—, wherein n is 1;

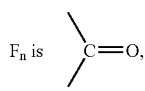

wherein n is 1
  $J_n$ is —CH$_2$—, wherein n is 1;
  $Z_n$ is —CH$_2$—, wherein n is 1;

X is 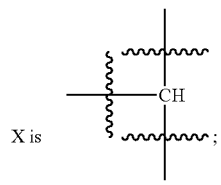

and
  $R^3$, $R^9$, $R^{10}$ and $R^{11}$ are H.

In another embodiment, this invention discloses a compound of the Formula:

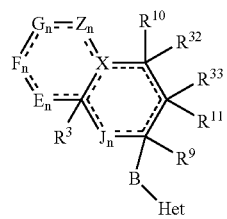

or a pharmaceutically acceptable salt, solvate, ester, or prodrug thereof, wherein
  Het is W-substituted pyridyl;
  W is phenyl substituted by at least one halogen or at least one cyano;

B is 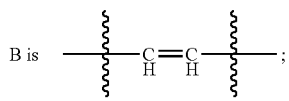

$E_n$ is —O—, wherein n is 1;
$G_n$ is —CH$_2$—, wherein n is 1;

$F_n$ is 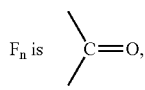

wherein n is 1
  $J_n$ is —CH$_2$—, wherein n is 1;
  $Z_n$ is —CH$_2$—, wherein n is 1;

X is 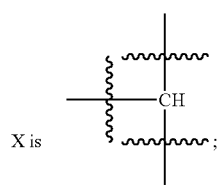

$R^3$, $R^9$, $R^{10}$ and $R^{11}$ are H; and
$R^{32}$ and $R^{33}$ are each methyl.

In another embodiment, this invention discloses a compound of the Formula:

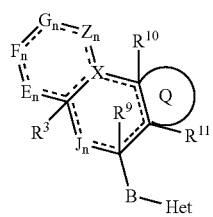

or a pharmaceutically acceptable salt, solvate, ester, or prodrug thereof, wherein Q is 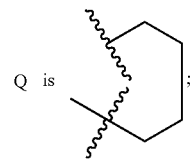

Het is W-substituted pyridyl;
W is phenyl substituted by at least one halogen or at least one cyano;

B is 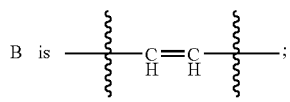

$E_n$ is 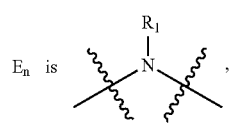

wherein n is 1;
  $G_n$ is —CH$_2$—, wherein n is 1;

$F_n$ is 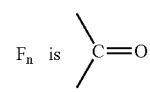

wherein n is 1
  $J_n$ is —CH$_2$—;
  $Z_n$ is —CH$_2$—;

X is 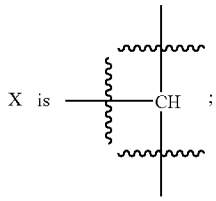

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and
$R^3$, $R^9$, $R^{10}$ and $R^{11}$ are H.

In another embodiment, this invention discloses a compound of the Formula:

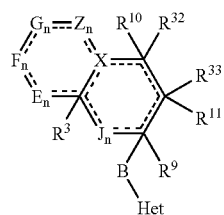

or a pharmaceutically acceptable salt, solvate, ester, or prodrug thereof, wherein Het is W-substituted pyridyl;

W is phenyl substituted by at least one halogen or at least one cyano;

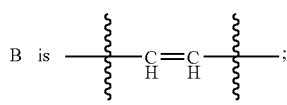

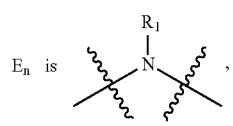

wherein n is 1

$G_n$ is —$CH_2$—, wherein n is 1;

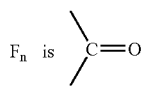

wherein n is 1

$J_n$ is —$CH_2$—;

$Z_n$ is —$CH_2$—,

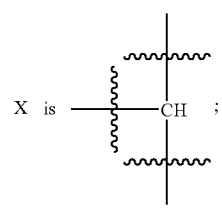

$R^3$, $R^9$, $R^{10}$ and $R^{11}$ are H;

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^{32}$ and $R^{33}$ are each methyl.

In another embodiment, this invention discloses a compound of the Formula:

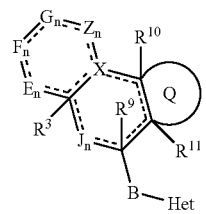

or a pharmaceutically acceptable salt, solvate, ester, or prodrug thereof, wherein

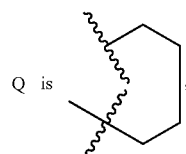

Het is W-substituted pyridyl;

W is phenyl substituted by at least one halogen or at least one cyano;

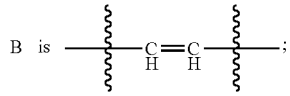

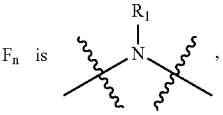

wherein n is 1;

$E_n$ is —$CH_2$, wherein n is 1;

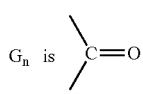

wherein n is 1

$J_n$ is —$CH_2$—;

$Z_n$ is —$CH_2$—;

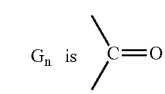

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^3$, $R^9$, $R^{10}$ and $R^{11}$ are H.

In another embodiment, this invention discloses a compound of the Formula:

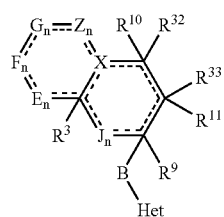

or a pharmaceutically acceptable salt, solvate, ester, or prodrug thereof, wherein Het is W-substituted pyridyl;

W is phenyl substituted by at least one halogen or at least one cyano;

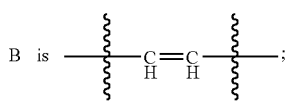

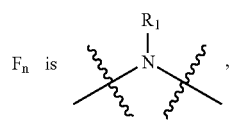

wherein n is 1;

$E_n$ is —$CH_2$—, wherein n is 1;

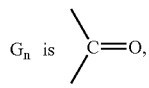

wherein n is 1

$J_n$ is —$CH_2$—, wherein n is 1;

$Z_n$ is —$CH_2$—, wherein n is 1;

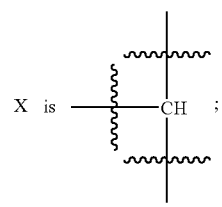

$R^3$, $R^9$, $R^{10}$ and $R^{11}$ are H;

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^{32}$ and $R^{33}$ are each methyl.

In another embodiment, this invention discloses a compound of the Formula.

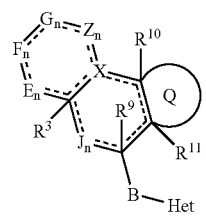

or a pharmaceutically acceptable salt, solvate, ester, or prodrug thereof, wherein

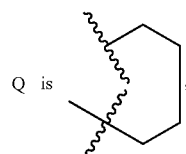

Q is

Het is W-substituted pyridyl;

W is phenyl substituted by at least one halogen or at least one cyano;

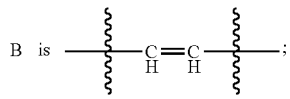

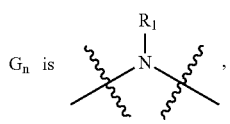

wherein n is 1

$E_n$ is —$CH_2$—, wherein n is 1;

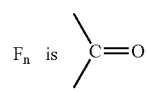

wherein n is 1

$J_n$ is —$CH_2$—;

$Z_n$ is —$CH_2$—;

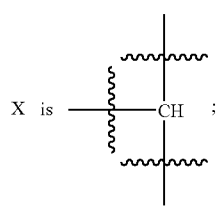

$R^1$ is selected from the group consisting of hydrogen, alkyl, fluoroalkyl, difluoroalkyl, trifluoroalkyl; cycloalkyl; alkenyl, alkoxy, arylalkyl; arylalkenyl, heteroarylalkyl, heteroarylalkenyl, hydroxy, hydroxyalkyl, alkoxyalkyl, aminoalkyl, aryl and thioalkyl; and $R^3$, $R^9$, $R^{10}$ and $R^{11}$ are H.

In another embodiment, this invention discloses a compound of the Formula:

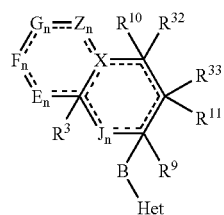

or a pharmaceutically acceptable salt, solvate, ester, or pro-drug thereof, wherein Het is W-substituted pyridyl;

W is phenyl substituted by at least one halogen or at least one cyano;

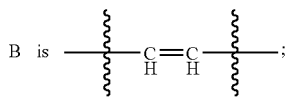

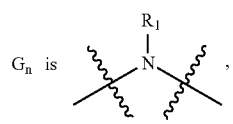

wherein n is 1;

$E_n$ is —CH$_2$—, wherein n is 1;

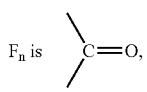

wherein n is 1

$J_n$ is —CH$_2$—, wherein n is 1;

$H_n$ is —CH$_2$—, wherein n is 1;

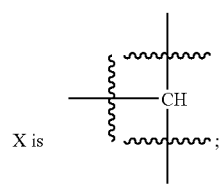

$R^3$, $R^9$, $R^{10}$ and $R^{11}$ are H;

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^{32}$ and $R^{33}$ are each methyl.

In another embodiment, this invention discloses a compound of the Formula:

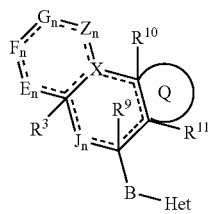

or a pharmaceutically acceptable salt, solvate, ester, or pro-drug thereof, wherein

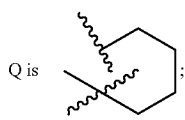

Het is W-substituted pyridyl;

W is phenyl substituted by at least one halogen or at least one cyano;

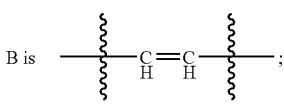

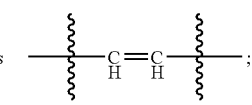

wherein n is 1;

$E_n$ is —O—, wherein n is 1;

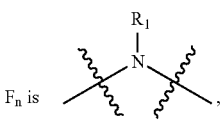

wherein n is 1

$J_n$ is —CH$_2$, wherein n is 1-;

$Z_n$ is —CH$_2$—, wherein n is 1;

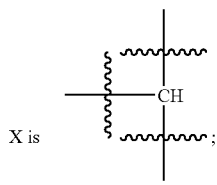

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^3$, $R^9$, $R^{10}$ and $R^{11}$ are H.

In another embodiment, this invention discloses a compound of the Formula:

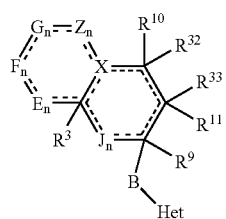

or a pharmaceutically acceptable salt, solvate, ester, or prodrug thereof, wherein Het is W-substituted pyridyl;

W is phenyl substituted by at least one halogen or at least one cyano;

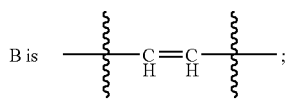

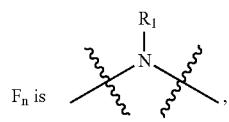

wherein n is 1;

$E_n$ is —O—, wherein n is 1;

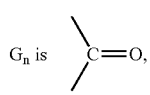

wherein n is 1

$J_n$ is —CH$_2$—, wherein n is 1;

$Z_n$ is —CH$_2$—, wherein n is 1;

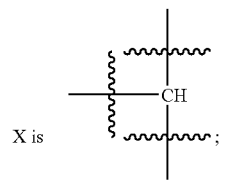

$R^3$, $R^9$, $R^{10}$ and $R^{11}$ are H;

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^{32}$ and $R^{33}$ are each methyl.

In another embodiment, this invention discloses a compound of the Formula:

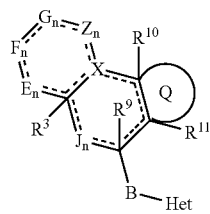

or a pharmaceutically acceptable salt, solvate, ester, or prodrug thereof, wherein

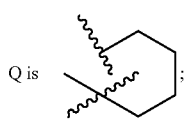

Het is W-substituted pyridyl;

W is phenyl substituted by at least one halogen or at least one cyano;

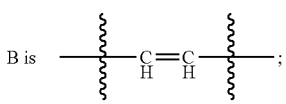

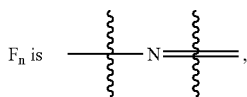

wherein n is 1;

$E_n$ is —O—, wherein n is 1;

$G_n$ is $G_0$;

$J_n$ is —CH$_2$—, wherein n is 1;

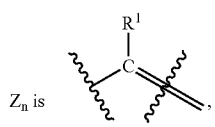

wherein n is 1;

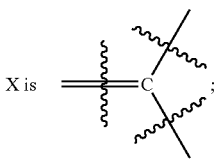

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^3$, $R^9$, $R^{10}$ and $R^{11}$ are H.

In another embodiment, this invention discloses a compound of the Formula.

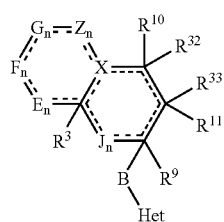

or a pharmaceutically acceptable salt, solvate, ester, or prodrug thereof, wherein Het is W-substituted pyridyl;

W is phenyl substituted by at least one halogen or at least one cyano;

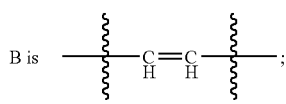

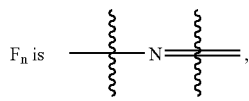

wherein n is 1;

$E_n$ is —O—, wherein n is 1;
$G_n$ is $G_0$;
$J_n$ is —CH$_2$—, wherein n is 1

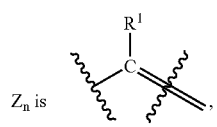

wherein n is 1;

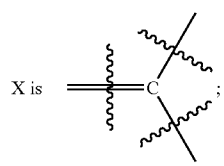

$R^3$, $R^9$, $R^{10}$ and $R^{11}$ are H;

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^{32}$ and $R^{33}$ are each methyl In another embodiment, this invention discloses a compound of the Formula:

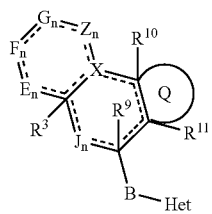

or a pharmaceutically acceptable salt, solvate, ester, or prodrug thereof, wherein

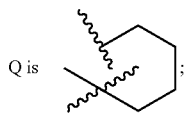

Het is W-substituted pyridyl;
W is phenyl substituted by at least one halogen or at least one cyano;

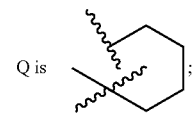

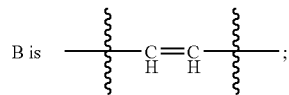

wherein n is 1;

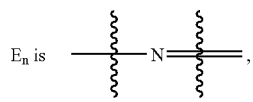

wherein n is 1
$G_n$ is $G_0$;
$J_n$ is —CH$_2$—, wherein n is 1;

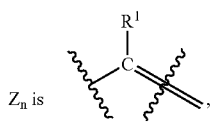

wherein n is 1;

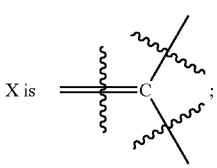

$R^1$ is selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^3$, $R^9$, $R^{10}$ and $R^{11}$ are H.

In another embodiment, this invention discloses a compound of the Formula:

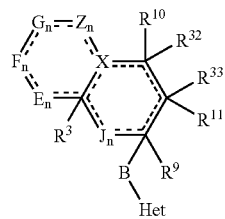

or a pharmaceutically acceptable salt, solvate, ester, or prodrug thereof, wherein Het is W-substituted pyridyl;

W is phenyl substituted by at least one halogen or at least one cyano;

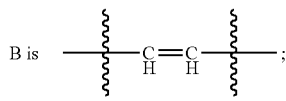

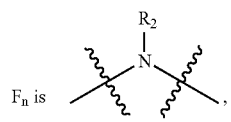

wherein n is 1;

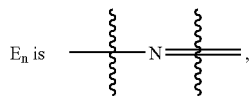

wherein n is 1;
$G_n$ is $G_0$;
$J_n$ is —CH$_2$—, wherein n is 1;

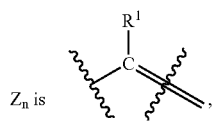

wherein n is 1;

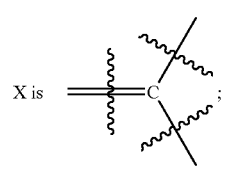

$R^3$, $R^9$, $R^{10}$ and $R^{11}$ are H;
$R^1$ and $R^2$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^{32}$ and $R^{33}$ are each methyl, In another embodiment, this invention discloses a compound of the Formula:

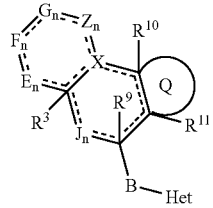

or a pharmaceutically acceptable salt, solvate, ester, or prodrug thereof, wherein

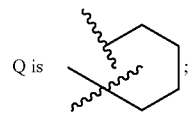

Het is W-substituted pyridyl,

W is phenyl substituted by at least one halogen or at least one cyano;

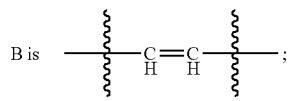

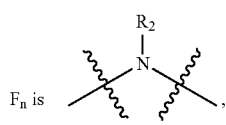

wherein n is 1;

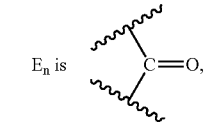

wherein n is 1;

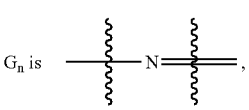

wherein n is 1
$J_n$ is —CH$_2$—, wherein n is 1;

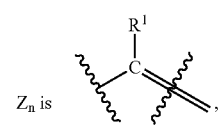

wherein n is 1;

X is 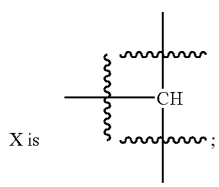;

R¹ and R² are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^3$, $R^9$, $R^{10}$ and $R^{11}$ are H.

In another embodiment, this invention discloses a compound of the Formula:

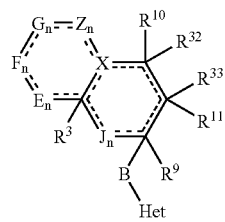

or a pharmaceutically acceptable salt, solvate, ester, or prodrug thereof, wherein Het is W-substituted pyridyl;

W is phenyl substituted by at least one halogen or at least one cyano;

B is 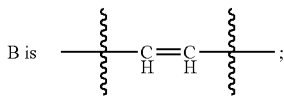;

$F_n$ is 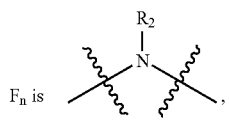, wherein n is 1;

$E_n$ is 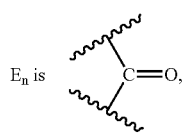, wherein n is 1;

$G_n$ is 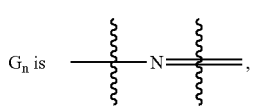, wherein n is 1

$J_n$ is —CH₂—, wherein n is 1;

$Z_n$ is 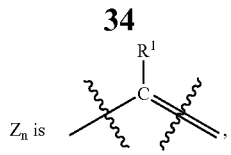, wherein n is 1;

X is 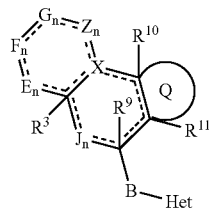;

$R^3$, $R^9$, $R^{10}$ and $R^{11}$ are H;

R¹ and R² are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and $R^{32}$ and $R^{33}$ are each methyl.

In another embodiment, this invention discloses a compound of the Formula:

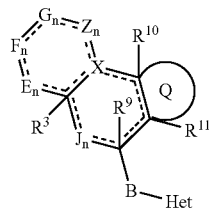

or a pharmaceutically acceptable salt, solvate, ester, or prodrug thereof wherein Q is

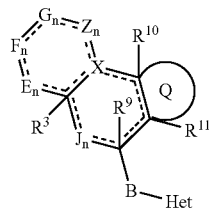;

Het is W-substituted pyridyl;

W is phenyl substituted by at least one halogen or at least one cyano;

B is 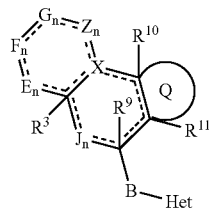;

$F_n$ is 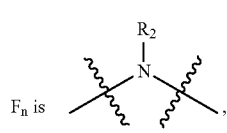, wherein n is 1;

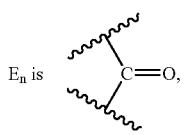

wherein n is 1;

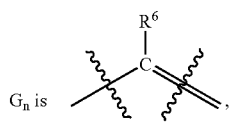

wherein n is 1;

$J_n$ is —CH$_2$—, wherein n is 1;

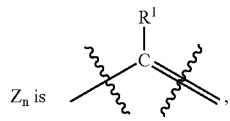

wherein n is 1;

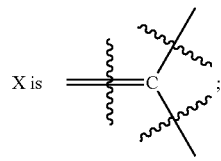

R$^1$ and R$^2$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl;

R$^6$ is hydrogen, alkyl, or phenyl and

R$^3$, R$^9$, R$^{10}$ and R$^{11}$ are H.

In another embodiment, this invention discloses a compound of the Formula:

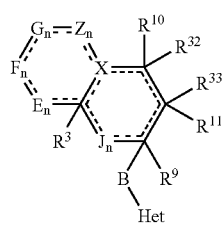

or a pharmaceutically acceptable salt, solvate, ester, or prodrug thereof, wherein Het is W-substituted pyridyl;

W is phenyl substituted by at least one halogen or at least one cyano;

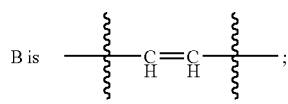

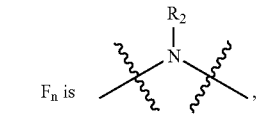

wherein n is 1;

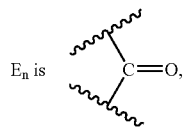

wherein n is 1;

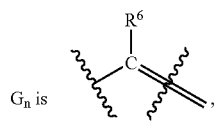

wherein n is 1

$J_n$ is —CH$_2$—, wherein n is 1;

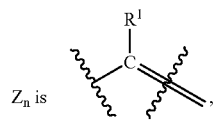

wherein n is 1;

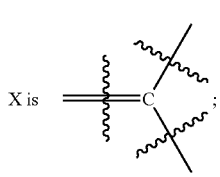

R$^3$, R$^9$, R$^{10}$ and R$^{11}$ are H;

R$^1$ and R$^2$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl;

R$^6$ is hydrogen, alkyl, or phenyl and

R$^{32}$ and R$^{33}$ are each methyl.

In another embodiment, this invention discloses a compound of the Formula:

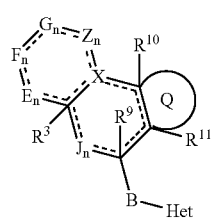

or a pharmaceutically acceptable salt, solvate, ester, or pro-drug thereof, wherein

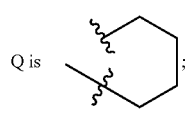

Het is W-substituted pyridyl;
W is phenyl substituted by at least one halogen or at least one cyano;

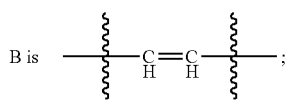

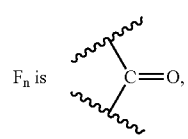

wherein n is 1;
$E_n$ is —O—, wherein n is 1;
$G_n$ is $G_0$;
$J_n$ is —$CH_2$—, wherein n is 1;

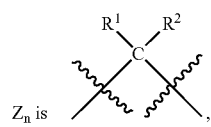

wherein n is 1;

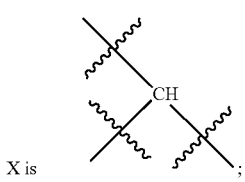

$R^1$ and $R^2$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl, and
$R^3$, $R^9$, $R^{10}$ and $R^{11}$ are H.

In another embodiment, this invention discloses a compound of the Formula:

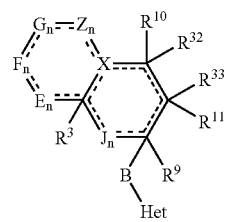

or a pharmaceutically acceptable salt, solvate, ester, or pro-drug thereof, wherein
Het is W-substituted pyridyl;
W is phenyl substituted by at least one halogen or at least one cyano;

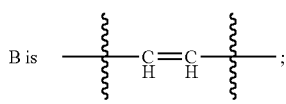

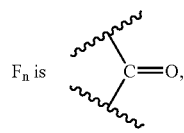

wherein n is 1;
$E_n$ is —O—, wherein n is 1;
$G_n$ is $G_0$;
$J_n$ is —$CH_2$—, wherein n is 1;

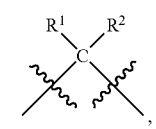

wherein n is 1;

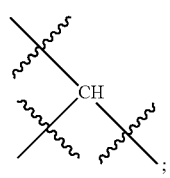

$R^3$, $R^9$, $R^{10}$ and $R^{11}$ are H;
$R^1$ and $R^2$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; and
$R^{32}$ and $R^{33}$ are each methyl.
Non-limiting examples of compounds of Formula I include:

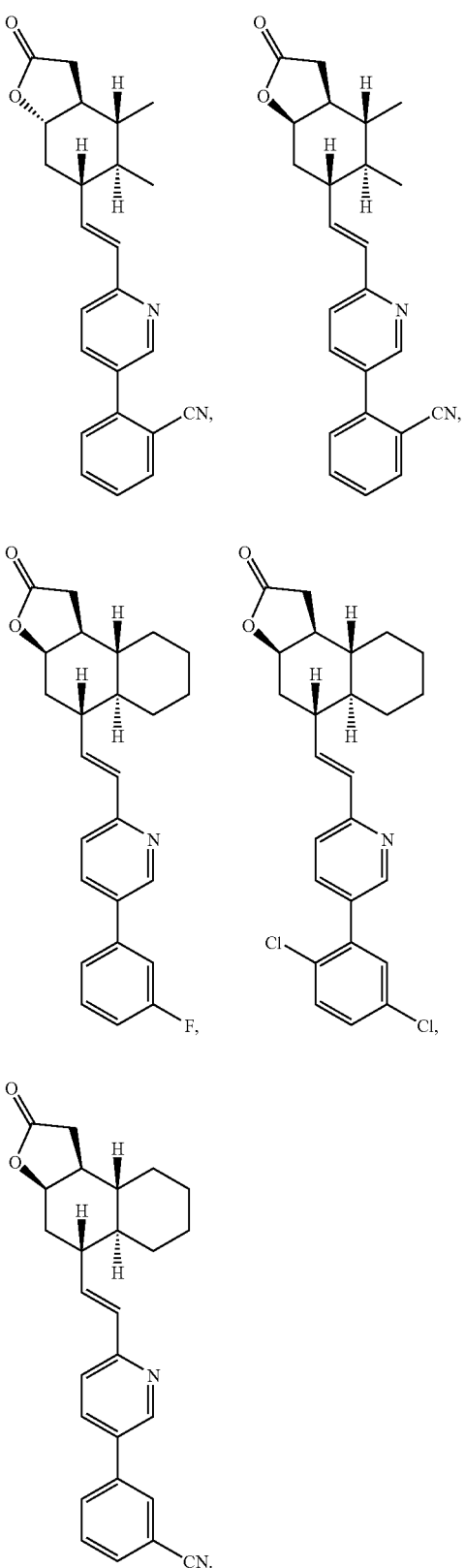

As used above, and throughout this disclosure, the following terms, unless otherwise indicated, shall be understood to have the following meanings:

"Patient" includes both human and animals.

"Subject" includes both mammals and non-mammalian animals.

"Mammal"' means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl, n-pentyl, heptyl, nonyl, decyl, fluoromethyl, trifluoromethyl, and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyd, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

The term "Het" is exemplified by the single ring, bicyclic and benzofused heteroaryl groups as defined immediately above. Het groups are joined to group B by a carbon ring member, e.g., Het is 2-pyridyl, 3-pyridyl or 2-quinolyl. The Het ring can be substituted on any available ring carbon by a group W; 1 to 4 W substituents can be present on a Het ring.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkylene" refers to a corresponding bivalent ring, wherein the points of attachment to other groups include all positional isomers.

"Dihydroxyalkyl" refers to an alkyl chain substituted by two hydroxy groups on two different carbon atoms.

"Fluoroalkyl", "difluoroalkyl" and "trifluoroalkyl" mean alkyl chains wherein the terminal carbon is substituted by 1, 2 or 3 fluoroatoms, respectively, e.g., —CF$_3$, —CH$_2$CF$_3$, —CH$_2$CHF$_2$ or —CH$_2$CH$_2$F.

"Halo" refers to fluorine, chlorine, bromine or iodine radicals. Preferred are fluoro, chloro or bromo, and more preferred are fluoro and chloro.

"Cycloalkenylalkyl" means a cycloalkenyl moiety as defined above linked via an alkyl moiety (defined above) to a parent core. Non-limiting examples of suitable cycloalkenylalkys include cyclopentenylmethyl, cyclohexenylmethyl and the like.

"Halo" refers to fluorine, chlorine, bromine or iodine radicals. Preferred are fluoro, chloro or bromo, and more preferred are fluoro and chloro.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

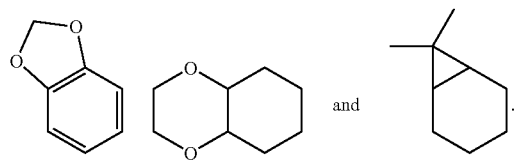

The term "Boc" refers to N-tert-butoxycarbonyl.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

"Heterocyclylalkyl" or "heterocycloalkylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or SS-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system.

Example of such moiety is pyrrolidinone:

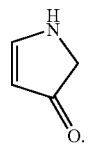

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

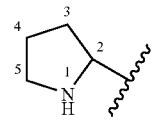

there is no —OH attached directly to carbons marked 2 and 5.

It should also be noted that tautomeric forms such as, for example, the moieties:

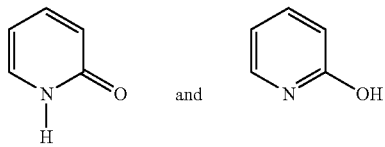

are considered equivalent in certain embodiments of this invention.

The term "heterospirocyclic" refers to a spirocyclic structure containing 3 to 5 carbon atoms and 1 or 2 heteroatoms selected from the group consisting of N, S and O, provided that the heteroatoms are not adjacent.

"Alkylamino" means an alkyl-amino group in which the alkyl group is as previously described. The bond to the parent moiety is through the amino.

"Alkylaminoalkyl" means an alkyl-amino-alkyl group in which the alkyl groups are as previously described. The bond to the parent moiety is through the alkyl.

"Alkylcycloalkylalkyl" means an alkyl-cycloalkyl-alkyl group in which the alkyl and cycloalkyl groups are as previously described. The bond to the parent moiety is through the alkyl.

"Alkylheteroaryl" means an alkyl-heteroaryl group in which the alkyl and heteroaryl groups are as previously described. The bond to the parent moiety is through the heteroaryl.

"Alkylheterocycloalkyl" means an alkyl-heterocycloalkyl group in which the alkyl and heterocycloalkyl groups are as previously described. The bond to the parent moiety is through the heterocycloalkyl group.

"Alkoxyalkyloxyalkyl" means an alkoxy-alkyl-O-alkyl group in which the alkoxy and alkyl groups are as previously described. The bond to the parent moiety is through the alkyl group.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Haloalkyl" means a halo-alkyl- group in which the alkyl group is as previously described. The bond to the parent moiety is through the alkyl. Non-limiting examples of suitable haloalkyl groups include fluoromethyl and difluoromethyl.

"Heteroarylalkenyl" means a heteroaryl-alkenyl group in which the heteroaryl and alkenyl are as previously described. Preferred heteroarylalkenyl contain a lower alkenyl group. The bond to the parent moiety is through the alkenyl group.

"Heterocycloalkyloxy" means a heterocycloalkyl-O— group in which the heterocycloalkyl group is as previously described. The bond to the parent moiety is through the ether atom.

"Heteroarylalkoxyalkyl" means a heteroaryl-alkoxyalkyl group in which the heteroaryl and alkoxyalkyl groups are as described above. The bond to the parent moiety is through the alkyl group, "Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Aminoalkyl" means an amino-alkyl group in which the alkyl group is as previously described. The bond to the parent moiety is through the alkyl.

"Alkenyloxy" means an alkenyl-O— group in which the alkenyl group is as previously described. The bond to the parent moiety is through the ether oxygen.

"Alkynyloxy" means an alkynyl-O— group in which the alkenyl group is as previously described. The bond to the parent moiety is through the ether oxygen.

"Aryloxyalkyl" means an aryl-O-alkyl group in which the aryl and alkyl groups are as previously described. Non-limiting examples of suitable aryloxyalkyl groups include phenoxymethyl and naphthoxymethyl. The bond to the parent moiety is through the alkyl group.

"Arylalkoxyalkyl" means an aryl-alkoxyalkyl group in which the aryl and alkoxyalkyl groups are as previously described. The bond to the parent moiety is through the alkyl group.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylsulfonyl" means an aryl-S(O$_2$)— group. The bond to the parent moiety is through the sulfonyl.

"Cycloalkenyloxy" means a cycloalkenyl-O— group in which the cycloalkenyl group is as previously described. The bond to the parent moiety is through the ether atom.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Cycloalkyloxy" or "cycloalkoxy" means a cycloalkyl-O— group in which the cycloalkyl group is as previously described. The bond to the parent moiety is through the ether atom.

"Cycloalkyloxyalkyl" means a cycloalkyl-O-alkyl group in which the cycloalkyl and alkyl groups are as previously described. The bond to the parent moiety is through the alkyl group.

"Haloalkoxyalkyl" means a halo alkoxyalkyl group in which the alkoxyalkyl group is as previously described. The bond to the parent moiety is through the alkyl group.

"Heterocyclylalkoxyalkyl" means a heterocyclyl-alkoxyalkyl group in which the alkoxyalkyl group is as previously described. The bond to the parent moiety is through the alkyl group.

The optional double bond represented by ---- means that at least a single bond must be present, but that a double bond can be present; when the double bond is present, $R^{10}$ is absent.

When $R^4$ and $R^5$ join to form a ring with the nitrogen to which they are attached, the rings formed are 1-pyrrolidinyl, 1-piperidinyl and 1-piperazinyl, wherein the piperazinyl ring may also be substituted at the 4-position nitrogen by a group $R^7$.

The above statements, wherein, for example, $R^4$ and $R^5$ are said to be independently selected from a group of substituents, means that $R^4$ and $R^5$ are independently selected when attached to the same nitrogen, but also that where an $R^4$ or $R^5$ variable occurs more than once in a molecule, those occurrences are independently selected. Similarly, each occurrence of $R^{13}$ or $R^{14}$ is independent of any other $R^{13}$ or $R^{14}$ in the same Q ring. Those skilled in the art will recognize that the size and nature of the substituent(s) will affect the number of substituents which can be present.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

The structure ----- in the compound of formula I, represents an optional double bond, the dotted line is a bond or no bond, resulting in a double bond or a single bond, as permitted by the valency requirement; with the proviso that $R^3$ is absent when the carbon to which $R^3$ would be attached is part of a double bond.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs, solvates, and co-crystals of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, t-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy $(C_1-C_6)$alkyl, amino $(C_1-C_4)$alkyl or mono-N— or di-N,N—$(C_0-C_6)$alkylaminoalkyl, —C(Y$^4$)Y$^5$ wherein Y$^4$ is H or methyl and Y$^5$ is mono-N— or di-N,N—$(C_1-C_5)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sc.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

A co-crystal is a crystalline superstructure formed by combining an active pharmaceutical intermediate with an inert molecule that produces crystallinity to the combined form. Co-crystals are often made between a dicarboxlyic acid such as fumaric acid, succinic acid etc. and a basic amine such as the one represented by compound I of this invention in different proportions depending on the nature of the co-crystal. (Rmenar, J. F. et. al. *J. Am. Chem. Soc.* 2003, 125, 8456).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prod rugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The compounds according to the invention have pharmacological properties; in particular, the compounds of Formula I can be nor-seco himbacine derivatives useful as thrombin receptor antagonists.

Compounds of the invention have at least one asymmetrical carbon atom and therefore all isomers, including enantiomers, stereoisomers, rotamers, tautomers and racemates of the compounds of Formula (I) (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of Formula I. Isomers may also include geometric isomers, e.g., when a double bond is present. Polymorphous forms of the compounds of Formula (I), whether crystalline or amorphous, also are contemplated as being part of this invention.

Typical preferred compounds of the present invention have the following stereochemistry:

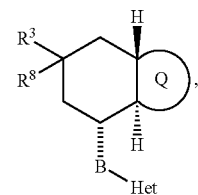

with compounds having that absolute stereochemistry being more preferred.

Those skilled in the art will appreciate that for some compounds of Formula I, one isomer will show greater pharmacological activity than other isomers.

Compounds of the invention are prepared from tricyclic intermediates by procedures known in the art; typical procedures are shown in Schemes 1 and 2, below.

Following are examples of preparing starting materials and compounds of formula I. In the procedures, the following abbreviations are used:

rt room temperature
THF tetrahydrofuran
$Et_2O$ ethyl ether
Me methyl
Et ethyl
EtOAc ethyl acetate
DCM Dichloromethane
DMF N,N-Dimethylformamide
DMAP Dimethylaminopyridine
LiHMDS or LHMDS:Lithium bis(trimethylsilyl)amide
$Ti(OiPr)_4$ titanium isopropoxide;
TLC thin layer chromatography
TMSI Trimethylsilyl iodide or iodotrimethylsilane Lactones such as 4 and 5 can be prepared from the ketone 2 as described in scheme 1. The ketone was alkylated with tert-butyl bromoacetate to provide intermediate 3 which was reduced with sodium borohydride then cyclized to provide the cis and trans lactams 4 and 5.

Scheme 1

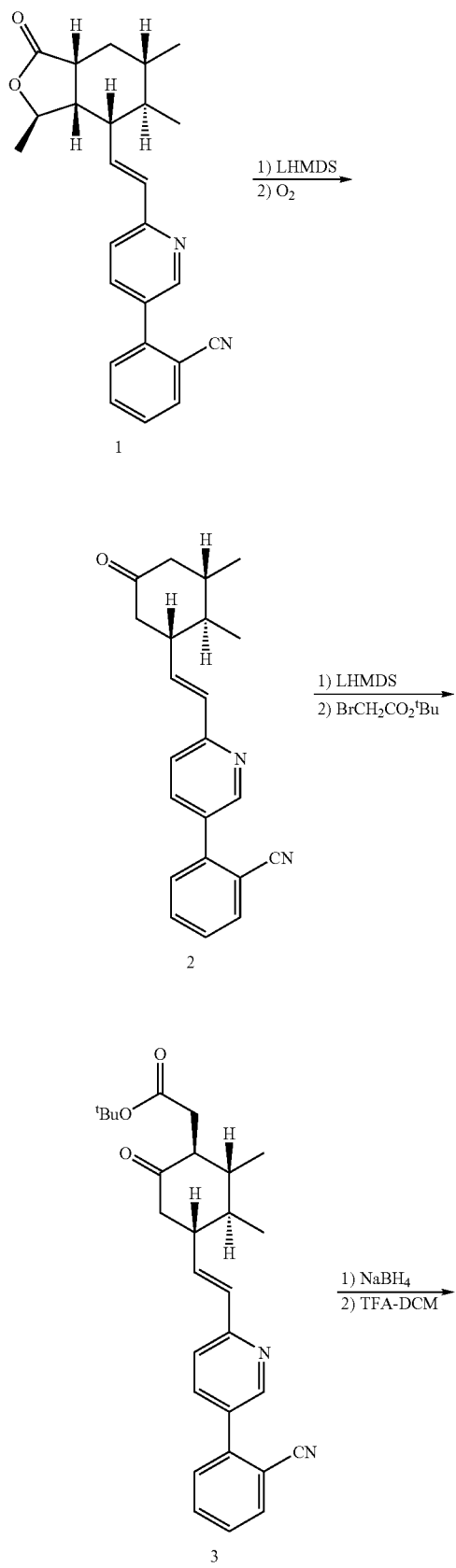

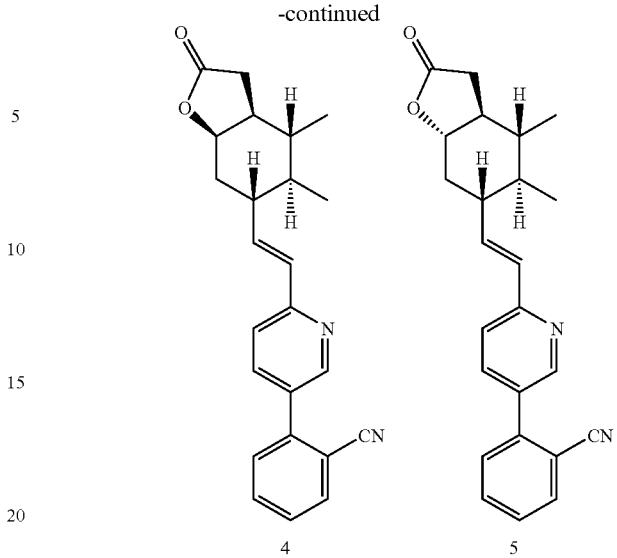

Preparation of 2

To a solution of 1 (9.0 g, 23.3 mmol) (see U.S. Patent 2004/0152736 A1 for the preparation of 1) in 150 ml THF at 0° C. was added LHMDS as a 1M solution in THF (35 ml, 35 mmol, 1.5 eq.). The mixture was stirred for 30 min. then evacuated and filled with oxygen using a balloon. The mixture was stirred under the oxygen atmosphere for 30 min at 0° C. and 1 hr at rt. The reaction was quenched by the addition of aqueous sodium sulfite, stirred for 1 hr and extracted with ethyl acetate. The crude product obtained was purified by silica gel chromatography to obtain 300 mg of 2 as a minor product.

MS: 331.1 (MH$^+$)

Preparation of 3

To a solution of 2 (160 mg, 0.48 mmol) in 5 ml THF at 0° C. was added a 1 M solution of LHMDS in THF (0.58 ml, 058 mmol, 1.2 eq) and after stirring for 10 min, tert-buytl bromoacetate was added. The mixture was stirred overnight while allowing warming to rt. It was quenched by the addition of aqueous ammonium chloride, extracted with ethyl acetate and the crude product was purified by preparative TLC using 30% ethyl acetate in hexanes to provide 36 mg of 3.

Preparation of 4 and 5

To a solution of 3 (43 mg, 0.097 mmol) in 1 ml methanol at 0 PC was added NaBH$_4$ (4 mg, 0.106 mmol, 1.0 eq.) and stirred for 10 min. The reaction was quenched by the addition of aqueous ammonium chloride and extracted with ethyl acetate to give 45 mg of crude product. This crude product was stirred with 0.5 ml each of dichloromethane and triftuoroacetic acid at rt for 2.5 hr. The solution was concentrated and the crude product was purified by preparative TLC using 35% ethyl acetate in hexanes to provide 16 mg of 4 and 21 mg of 5.

MS for 4: 373.1 (MH$^+$)
MS for 5: 373.1 (MH$^+$)

An alternate approach to the preparation of these types of compounds is described in scheme 2. Carboxylic acid 6 was converted to the aldehyde 8 via the alcohol 7. Horner-Wordsworth reaction with phosphonate 9 gave the vinyl pyridine 10 which was α-hydroxylated to II. Reduction of the lactone to the lactol followed by reaction with Dess-Martin periodinane reagent gave formate 13 which under basic conditions gave the ketone 14. Alkylation with tert-butyl bromoacetate gave intermediates 15 and 16. Ketone 16 was reduced to the axial alcohol with L-selectride and cyclized to the lactone 17 under acidic conditions. Suzuki coupling of 17 gave the target compounds 18-20.

Scheme 2
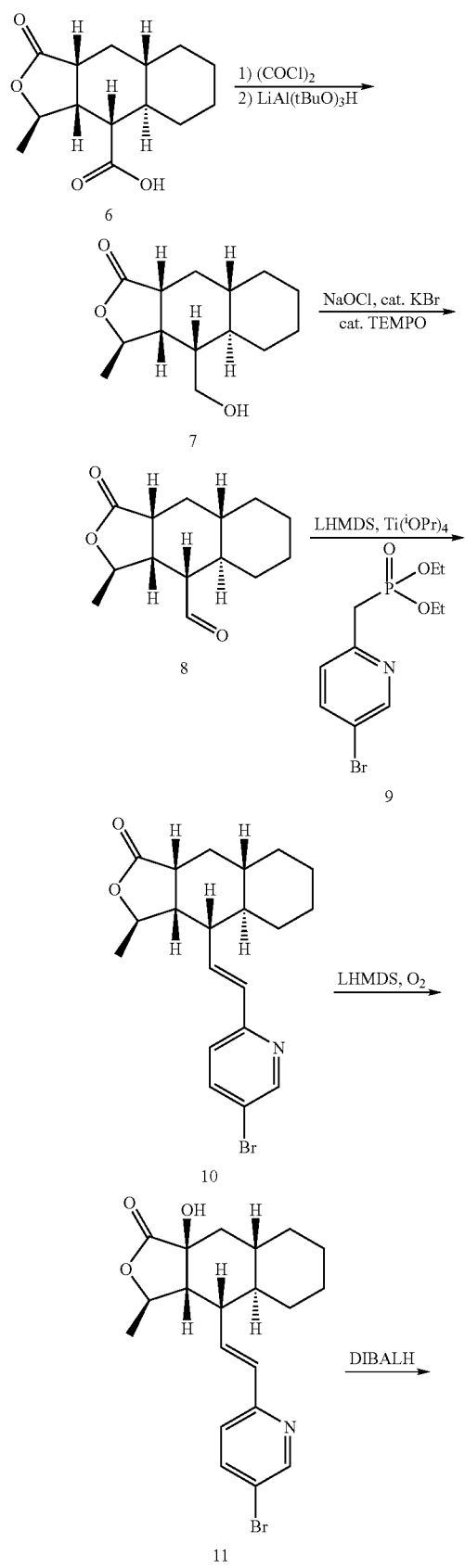
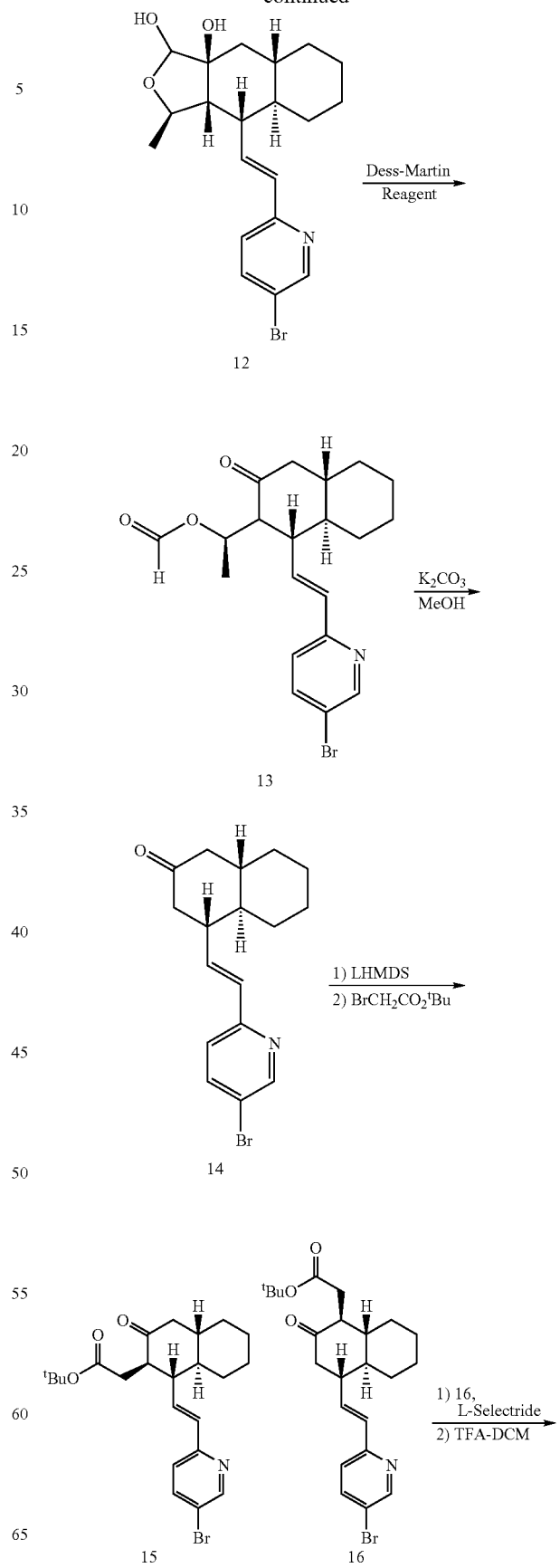

Preparation of 7

To a solution of 6 (30 g, 0.119 mol) (see U.S. Pat. No. 6,063,847 for the preparation of 6) in 400 ml dichloromethane was added oxalyl chloride (21 ml, 0.241 mol. 2 eq.) followed by DMF (275 µl, 3.55 mmol, 5 mot %). The mixture was stirred for 2 hr, concentrated and evaporated with toluene to provide the acid chloride. This was dissolved in 500 ml THF, cooled to 0° C., added lithium tri-ter-butoxyaluminohydride (76 g, 0.299 mol, 2.5 eq.) and the mixture was stirred for 2 hr. It was diluted with water, acidified with HCl, extracted with ethyl acetate to provide 21.6 g of 7,

Preparation of 8

To a solution of 7 (12.0 g, 50.4 mmol) in 200 ml dichloromethane at 0° C. was added 2,2,6,6-tetramethylpiperidinooxy (160 mg, 1.02 mmol, 2 mol %) and a solution of potassium bromide (600 mg, 5.04 mmol, 0.1 eq.) in 10 ml water. To this mixture was added drop by drop Clorox solution (92 9, ~6.15% NaOCl content) saturated with solid $NaHCO_3$. After the addition was complete, the mixture was stirred for 20 min, organic layer separated and the aqueous layer extracted with dichloromethane. The combined organic layer washed with aq. $Na_2S_2O_3$, brine, dried over $MgSO_4$, filtered and concentrated to provide 12 g of 8 as a resin.

Preparation of 10

To a solution of 9 (20 g, 65 mmol) (see U.S. Patent Application No. 2004/0152736 A1 for the preparation of 9) in 200 ml THF at 0° C. was added a 1 M solution of LHMDS in THF (65 ml, 65 mmol) and the mixture stirred for 30 min at 0° C. To this was added $Ti(OPr)_4$ (22.3 ml, 75.5 mmol) followed by a solution of aldehyde 8 (12 g) in 50 ml THF. The mixture was stirred for 15 min at 0° C. and 30 min at rt then quenched with aq. $NH_4Cl$, Ethyl acetate extraction followed by chromatographic purification using 0% to 15% ethyl acetate-hexanes gave 3.3 g of 10.

Preparation of 11

To a solution of 10 (3.3 g, 8.46 mmol) in 50 ml THF at 0° C. was added a 1M solution of LHMDS in THF (12.7 ml, 12.7 mmol, 1.5 eq.) and stirred for 30 min. The flask was evacuated and filled with oxygen and stirred under the oxygen atmosphere for 1 hr at rt. It was quenched by the addition of aq. $Na_2SO_3$, stirred for 30 min. extracted with ethyl acetate and purified by chromatography using 0% to 20% ethyl acetate-hexanes to provide 3 g of 11.

MS: 406.1 ($MH^+$)

Preparation of 12

To a solution of 11 (4.2 g, 10.3 mmol) in 75 ml dichloromethane at −78° C. was added a 20 wt % solution of DIBALH in toluene (34.2 mmol, 41.4 mmol, 4 eq.) and stirred for 1 hr at −78° C. It was quenched by the addition of aq. potassium sodium tartrate and extracted with dichloromethane to provide 2.89 g of 12.

MS; 408.22 ($MH^+$)

Preparation of 13

To a solution of 12 (2.89 g, 7.08 mmol) in 50 ml dichloromethane at rt was added $NaHCO_3$ (1.2 g, 14.28 mmol, 2 eq.) followed by Dess-Martin periodinane (3.90 g, 9.19 mmol, 1.3 eq.) and the suspension was stirred for 2 hr. The reaction mixture was diluted with ether and stirred with aq. $Na_2S_2O_3$ and $NaHCO_3$ until the two layers became clear. The organic layer was separated and the aqueous layer was extracted with ether. The combined organic layer washed with aq. $Na_2S_2O_3$, $NaHCO_3$ mixture and brine. The solution was dried over $MgSO_4$, filtered, concentrated and evaporated to provide ~3.0 g of 13.

MS. 406.2 ($MH^+$)

Preparation of 14

A solution of 14 (~7.08 mmol) in 50 ml methanol was stirred with $K_2CO_3$ (3.9 g, 28.2 mmol, 4 eq.) at rt for 3 hr and diluted with water. It was extracted with ether and the crude product was chromatographed using 0% to 100% ethyl acetate—hexanes to provide 1.74 g of 14.

MS: 334.1 ($MH^+$)

Preparation of 16

To a solution of 14 (1.39 g, 4.15 mmol) in 30 ml THF at 0° C. was added a 1 M solution of LHMDS in THF (5.0 ml, 5.0 mmol, 1.2 eq.) and stirred for 30 min then added tert-butyl bromoacetate (0.92 ml, 6.23 mmol, 1.5 eq.) and the mixture stirred overnight allowing to warm to rt. The solution was diluted with aq. $NH_4Cl$, extracted with ethyl acetate and the crude product was purified by chromatography to provide 920 mg of 15 and 420 mg of 16 which contains about 20% of 14.

MS for 15: 448.1 ($MH^+$)

MS for 16: 448.1 ($MH^+$)

Preparation of 17

To a solution of 16 (420 mg, 0.937 mmol) in 10 ml THF at −78° C. was added 1 M solution of L-selectride in THF (2.8 ml, 2.8 mmol, 3 eq) and the mixture stirred for 1 hr at −78° C. The reaction was quenched with the addition of few drops of acetone and stirred for few minutes at rt. The solvent was concentrated to dryness and the residue was stirred with 5 ml of dichloromethane and 10 ml of trifluoroacetic acid and stirred at rt for 2 hr. The solvent Was concentrated and taken in aq. $NaHCO_3$. It was extracted with ethyl acetate and purified by chromatography using 0% to 20% ethyl acetate—hexanes to provide 80 mg of 17.

MS: 376.2 ($MH^+$)

Preparation of 18

A solution of 17 (25 mg, 0.066 mmol), m-fluorophenylboronic acid (19 mg, 0.136 mmol, 2 eq.), $K_2CO_3$ (37 mg, 0.268 mmol, 4 eq.) and $Pd(PPh_3)_4$ (4 mg, 3.5 µmol, 5 mol) in a mixture of 0.7 ml toluene, 0.3 ml ethanol and 0.15 ml water was bubbled with argon and heated in a sealed tube at 100° C. for 5 hr. The solution was poured into water, extracted with ethyl acetate, dried over $MgSO_4$, filtered, concentrated and purified by preparative TLC using 10% ethyl acetate-dichloromethan to provide 6 mg of 18.

Compounds 19 and 20 were prepared using analogous procedures.

MS for 18: 392.1 ($MH^+$)
MS for 19: 442.1 ($MH^+$)
MS for 20: 399.1 ($MH^+$)

Further embodiments of the invention encompass the administration of compounds of Formula I along with at least one additional agent. The contemplated additional agent is one that differs in either atomic make up or arrangement from the compounds of Formula I. Additional agents that can be used in combination with the novel compounds of this invention include drugs that are useful in treating thrombosis-related diseases including thrombosis, atherosclerosis, restenosis, hypertension, angina pectoris, angiogenesis related disorders, arrhythmia, a cardiovascular or circulatory disease or condition, heart failure, myocardial infarction, glomerulonephritis, thrombotic stroke, thromboembolytic stroke, peripheral vascular diseases, cerebral ischemia, rheumatoid arthritis, rheumatism, astrogliosis, a fibrotic disorder of the liver, kidney, lung or intestinal tract, systemic lupus erythematosus, multiple sclerosis, osteoporosis, glomerulonephritis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy and/or malignant tumors, neurodegenerative and/or neurotoxic diseases, conditions, or injuries, inflammation, asthma, glaucoma, macular degeneration, psoriasis, endothelial dysfunction disorders of the liver, kidney or lung inflammatory disorders of the lungs and gastrointestinal tract, respiratory tract disease or condition, radiation fibrosis, endothelial dysfunction, periodontal diseases or wounds or a spinal cord injury, or a symptom or result thereof, as well as other disorders in which thrombin and its receptor play a pathological role.

Suitable cardiovascular agents are selected from the group consisting of thromboxane A2 biosynthesis inhibitors; thromboxane antagonists; adenosine diphosphate inhibitors; cyclooxygenase inhibitors; angiotensin antagonists; endothelin antagonists; phosphodiesterase inhibitors; angiotensin converting enzyme inhibitors; neutral endopeptidase inhibitors; anticoagulants; diuretics; platelet aggregation inhibitors; and GP IIb/IIIa antagonists.

Preferred types of drugs for use in combination with the novel compounds of this invention are thromboxane A2 biosynthesis inhibitors, GP IIb/IIIa antagonists, thromboxane antagonists, adenosine diphosphate inhibitors, cyclooxygenase inhibitors, angiotensin antagonists, endothelin antagonists, angiotensin converting enzyme inhibitors, neutral endopeptidase inhibitors, anticoagulants, diuretics, and platelet aggregation inhibitors.

In particular, suitable cardiovascular agents are selected from the group consisting of aspirin, seratrodast, picotamide and ramatroban, clopidogrel, meloxicam, rofecoxib, celecoxib, valsartan, telmisartan, candesartran, irbesartran, losartan, eprosartan, tezosentan, milrinoone, enoximone, captopril, enalapril, enatiprilat, spirapril, quinapril, perindopril, ramipril, fosinopril, trandolapril, lisinopril, moexipril, benazapril, candoxatril, ecadotril, ximelagatran, fondaparin, enoxaparin, chlorothiazide, hydrochlorothiazide, ethacrynic acid, furosemide, amiloride, abciximab, eptifibatide, parsugrel and fragmin.

Especially preferred for use in the combinations are aspirin, cangrelor, clopidogrel bisulfate, parsugrel and fragmin.

When the invention comprises a combination of a compound of Formula I and another agent, the two active components may be co-administered simultaneously or sequentially, or a single pharmaceutical composition comprising a compound of Formula I and another agent in a pharmaceutically acceptable carrier can be administered. The components of the combination can be administered individually or together in any conventional dosage form such as capsule, tablet, powder, cachet, suspension, solution, suppository, nasal spray, etc. The dosage of the additional agent can be determined from published material, and may range from 1 to 1000 mg per dose.

In this specification, the term "at least one compound of Formula I" means that one to three different compounds of Formula I may be used in a pharmaceutical composition or method of treatment. Preferably one compound of Formula I is used. Similarly, the term "one or more additional cardiovascular agents" means that one to three additional drugs may be administered in combination with a compound of Formula I; preferably, one additional compound is administered in combination with a compound of Formula I. The additional agents can be administered sequentially or simultaneously with reference to the compound of Formula I.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A, Gennaro (ed.), *The Science and Practice of Pharmacy*, $20^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When separate compounds of Formula I and the other agents are to be administered as separate compositions, they can be provided in a kit comprising in a single package, one container comprising a compound of Formula I in a pharmaceutically acceptable carrier, and a separate container comprising another cardiovascular agent in a pharmaceutically acceptable carrier, with the compound of Formula I and the other agent being present in amounts such that the combination is therapeutically effective. A kit is advantageous for administering a combination when, for example, the components must be administered at different time intervals or when they are in different dosage forms.

The activity of the compounds of formula I can be determined by the following procedures.

In Vitro Testing Procedure for Thrombin Receptor Antagonists

Preparation of [$^3$H]haTRAP

A(pF-F)R(ChA)(hR)(I$_2$—Y)—NH$_2$ (1.03 mg) and 10% Pd/C (5.07 mg) were suspended in DMF (250 µl) and diisopropylethylamine (10 µl). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H]haTRAP) was dissolved in 0.5 ml of 0.1% aqueous TFA and purified by HPLC using the following conditions: column, Vydac™ C18, 25 cm×9.4 mm I.D.; mobile phase, (A) 0.1% TFA in water, (B) 0.1% TFA in CH$_3$CN; gradient, (A/B) from 100‰ to 40‰ over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al. (Natarajan et al, *Int. J. Peptide Protein Res.* 45:145-151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were re-suspended in 10 mM Tris-HCl, pH 7.5, 150 mM NaCl, 5 mM EDTA, to a total volume of 200 ml and centrifuged at 4400×g for 10 minutes. This step was repeated two additional times. Platelets were re-suspended in 5 mM Tris-HCl, pH 7.5, 5 mM EDITA to a final volume of approximately 30 ml and were homogenized with 20 strokes in a Dounce™ homogenizer. Membranes were pelleted at 41,000×g, re-suspended in 40-50 ml 20 mM Tris-HCl, pH 7.5, 1 mM EDTA, 0.1 mM dithiothreitol, and 10 ml aliquots were frozen in liquid N$_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and re-suspended in 20-25 ml 50 mM Tris-HCl, pH 7.5, 10 mM MgCl$_2$, 1 mM EGTA, and 1% DMSO. Aliquots of membranes were frozen in liquid N$_2$ and stored at −80° C. Membranes were stable for at least 3 months. 20 units of platelet concentrates typically yielded 250 mg of membrane protein. Protein concentration was determined by a Lowry assay (Lowry et al., *J. Biol. Chem.*, 193:265-275 (1951)).

High Throughput Thrombin Receptor Radioligand Binding Assay

Thrombin receptor antagonists were screened using a modification of the thrombin receptor radioligand binding assay of Ahn et al. (Ahn et al., *Mol. Pharmacol*, 51:350-356 (1997)). The assay was performed in 96 well Nunc plates (Cat. No. 269620) at a final assay volume of 200 µl. Platelet membranes and [$^3$H]haTRAP were diluted to 0.4 mg/ml and 22.2 nM, respectively, in binding buffer (50 mM Tris-HCl, pH 7.5, 10 mM MgCl$_2$, 1 mM EGTA, 0.1% BSA). Stock solutions (10 mM in 100% DMSO) of test compounds were further diluted in 100% DMSO. Unless otherwise indicated, 10 µl of diluted compound solutions and 90 µl of radioligand (a final concentration of 10 nM in 5% DMSO) were added to each well, and the reaction was started by the addition of 100 µl of membranes (40 µg protein/well). The binding was not significantly inhibited by 5% DMSO. Compounds were tested at three concentrations (0.1, 1 and 10 µM). The plates were covered and vortex-mixed gently on a Lab-Line™ Titer Plate Shaker for 1 hour at room temperature. Packard UniFilter™ GF/C filter plates were soaked for at least 1 hour in 0.1% polyethyleneimine. The incubated membranes were harvested using a Packard FilterMate™ Universal Harvester and were rapidly washed four times with 300 µl ice cold 50 mM Tris-HCl, pH 7.5, 10 mM MgCl$_2$, 1 mM EGTA. MicroScint™ 20 scintillation cocktail (25 µl) was added to each well, and the plates were counted in a Packard TopCount™ Microplate Scintillation Counter. The specific binding was defined as the total binding minus the nonspecific binding observed in the presence of excess (50 µM) unlabeled haTRAP. The % inhibition by a compound of [$^3$H]haTRAP binding to thrombin receptors was calculated from the following relationship:

% Inhibition=Total binding-Binding in the presence of a test compound×100 Total binding-Nonspecific binding Materials A(pF-F)R(ChA)(hR)Y—NH$_2$ and A(pF-F)R(ChA)(hR)(I$_2$—Y)—NH$_2$, were custom synthesized by AnaSpec Inc.

(San Jose, Calif.). The purity of these peptides was >95%. Tritium gas (97%) was purchased from EG&G Mound, Miamisburg, Ohio. The gas was subsequently loaded and stored on an IN/US Systems Inc. Trisorber. MicroScint™ 20 scintillation cocktail was obtained from Packard Instrument Co.

Cannabinoid $CB_2$ Receptor Binding Assay

Binding to the human cannabinoid $CB_2$ receptor was carried out using the procedure of Showalter, et al. (1996, *J. Pharmacol Exp Ther.* 278(3), 989-99), with minor modifications. All assays were carried out in a final volume of 100 ul. Test compounds were re-suspended to 10 mM in DMSO, then serially diluted in 50 mM Tris, pH 7.1, 3 mM $MgCl_2$, 1 mM EDTA, 50% DMSO. Aliquots (10 ul) of each diluted sample were then transferred into individual wells of a 96-well microtiter plate. Membranes from human $CB_2$ transfected CHO/Ki cells (Receptor Biology, Inc) were re-suspended in binding buffer (50 mM Tris, pH 7.1, 3 mM $MgCl_2$, 1 mM EDTA, 0.1% fatty acid free bovine serum albumin), then added to the binding reaction (~15 ug in 50 ul per assay). The reactions were initiated with the addition of [$^3$H] CP-55, 940 diluted in binding buffer (specific activity=180 Ci/mmol; New England Nuclear, Boston, Mass.). The final ligand concentration in the binding reaction was 0.48 nM. Following incubation at room temperature for 2 hours, membranes were harvested by filtration through pretreated (0.5% polyethylenimine; Sigma P-3143) GF-C filter plates (Unifilter-96, Packard) using a TomTec™ Mach 3U 96-well cell harvester (Hamden, Conn.). Plates were washed 10 times in 100 ul binding buffer, and the membranes allowed to air dry. Radioactivity on membranes was quantitated following addition of Packard Omniscint™ 20 scintillation fluid using a TopCount™ NXT Microplate Scintillation and Luminescence Counter (Packard, Meriden, Conn.). Non-linear regression analysis was performed using Prism™ 20b. (GraphPad Software, San Diego, Calif.).

Using the test procedures described above, representative compounds of formula I were found to have thrombin receptor $K_i$ values ranging from about 3 nM to about 20 nM and thrombin receptor $IC_{50}$ values ranging from about 5 nM to about 70 nM as shown in Table 1 below.

TABLE I

| Compound No. | Structure | $K_i$ | $IC_{50}$ |
|---|---|---|---|
| 1 | | | 45 nM |
| 2 | 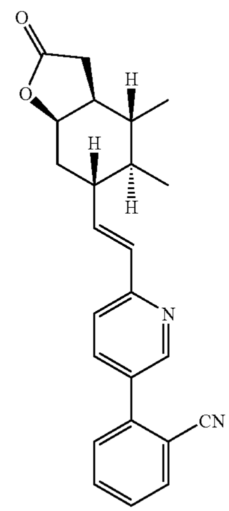 | 11 nM | 16 nM |
| 3 | 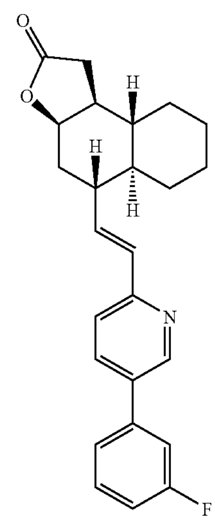 | 3.1 nM | 4.8 nM |
| 4 | 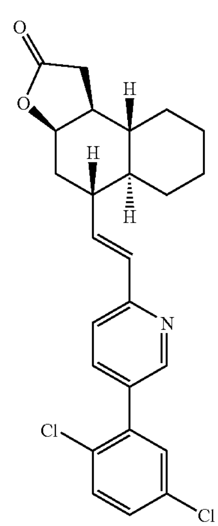 | 13 nM | 20 nM |

TABLE I-continued

| Compound No. | Structure | $K_i$ | $IC_{50}$ |
|---|---|---|---|
| 5 | 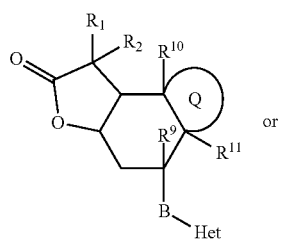 | 4.3 nM | 6.7 nM |

We claim:

1. A compound of Formula IK or Formula IIK

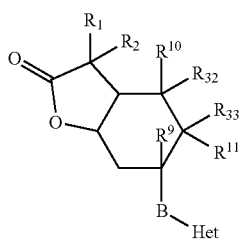

Ik

IIk or a pharmaceutically acceptable salt thereof wherein:

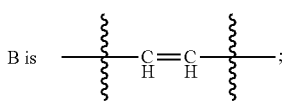

B is

Het is a pyridyl group wherein the pyridyl group is attached to B by a carbon atom ring member, and wherein the pyridyl group is substituted by 1 to 4 moieties, W, wherein each W is independently selected from the group consisting of:

hydrogen, alkyl, aryl or aryl substituted by 1 to 3 substituents independently selected from the group consisting of alkyl, halogen, alkoxy, —CN, —CF$_3$, —OCF$_3$ or —OH;

$R^1$ is hydrogen, alkyl, fluroalkyl, difluroralkyl or trifluroralkyl;

$R^2$ is hydrogen, alkyl, fluroalkyl, difluroralkyl or trifluroralkyl;

$R^9$ is hydrogen;

$R^{10}$ and $R^{11}$ are H or alkyl;

Q is 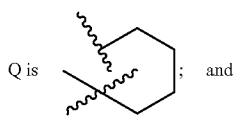 and $R^{32}$ and $R^{33}$ are H or alkyl.

2. The compound of claim 1 or a pharmaceutically acceptable salt thereof wherein $R^{32}$ and $R^{33}$, which can be the same or different, are each alkyl.

3. The compound of claim 1 or a pharmaceutically acceptable salt thereof, wherein $R^{32}$ and $R^{33}$ are each methyl.

4. The compound of claim 1 or a pharmaceutically acceptable salt thereof, wherein Q is

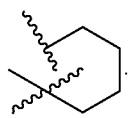

5. The compound of claim 1 or a pharmaceutically acceptable salt thereof, wherein W is phenyl, which is unsubstituted or substituted by a group selected from the group consisting of halogen or —CN.

6. The compound of claim 1 or a pharmaceutically acceptable salt thereof, wherein $R^9$, $R^{10}$ and $R^{11}$ are hydrogen.

7. A compound of the formula or a pharmaceutically acceptable salt thereof, which is:

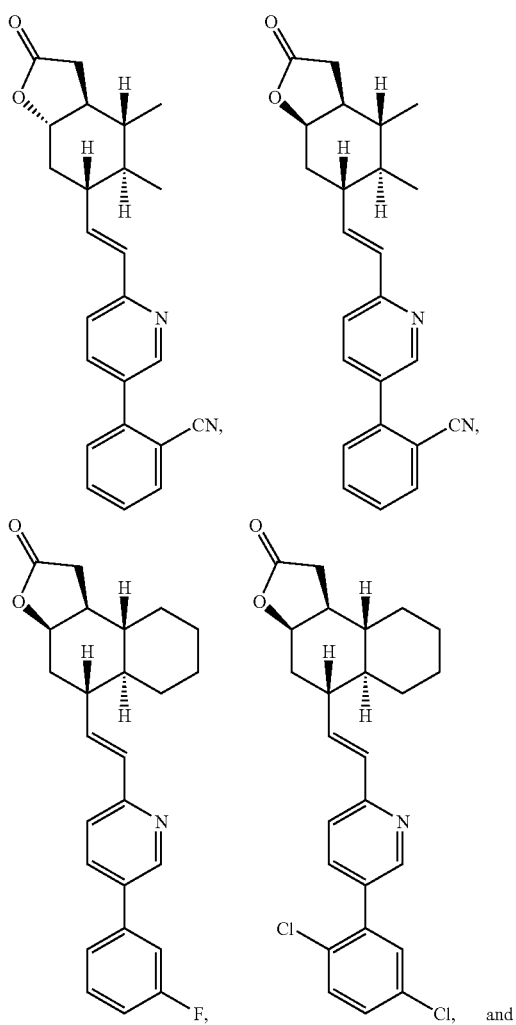
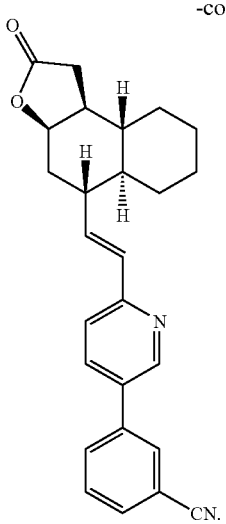
and
8. A pharmaceutical composition comprising an effective amount of at least one compound of claim 1 and a pharmaceutically acceptable carrier.
9. A compound of claim 1 or a pharmaceutically acceptable salt thereof in purified form.
10. A compound of claim 1 or a pharmaceutically acceptable salt thereof in isolated form.
* * * * *